US006728334B1

(12) United States Patent
Zhao

(10) Patent No.: US 6,728,334 B1
(45) Date of Patent: Apr. 27, 2004

(54) AUTOMATIC DETECTION OF PULMONARY NODULES ON VOLUMETRIC COMPUTED TOMOGRAPHY IMAGES USING A LOCAL DENSITY MAXIMUM ALGORITHM

(75) Inventor: Binsheng Zhao, Forest Hills, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/279,592

(22) Filed: Oct. 23, 2002

Related U.S. Application Data

(60) Provisional application No. 60/338,880, filed on Oct. 24, 2001.

(51) Int. Cl.[7] ........................... G01N 23/04; A61B 6/03

(52) U.S. Cl. ............................. 378/62; 378/4; 378/901; 382/131

(58) Field of Search ............................ 378/4, 8, 15, 62, 378/901; 382/131

(56) References Cited

U.S. PATENT DOCUMENTS

| | | | |
|---|---|---|---|
| 5,228,443 | A | 7/1993 | Tatar |
| 5,283,837 | A | 2/1994 | Wood |
| 5,289,374 | A | 2/1994 | Doi et al. |
| 5,351,067 | A | 9/1994 | Lumelsky et al. |
| 5,666,434 | A | 9/1997 | Nishikawa et al. |
| 5,712,926 | A | 1/1998 | Eberhard et al. |
| 5,825,936 | A | 10/1998 | Clarke et al. |
| 5,877,771 | A | 3/1999 | Drebin et al. |
| 6,205,350 | B1 | 3/2001 | Lorenz et al. |

FOREIGN PATENT DOCUMENTS

| | | |
|---|---|---|
| WO | 01-78005 | 10/2001 |

OTHER PUBLICATIONS

Author: Z.–H. Cho, J. P. Jones, and M. Singh, *Foundations of Medical Imaging.* John Wiley and Sons Inc.; Title: "X–Ray Computerized Tomography", pp. 148–164; Date of Publication: 1993; Place of Publication: U.S.

Author: A.K. Jain; Title: "Fundamentals of Digital Image Processing", Prentice Hall, Englewood Cliffs, NJ; pp. 384–389; Date Publication: 1989; Place of Publication: U.S.

Author: S. N. Reske, R. Bares, U. Bull, A. Guhlmann. E. Moser, and M. F. Wannemacher; Title: "[Clinical value of positron emission tomography (PET) in oncologic questions: results of an interdisciplinary consensus conference. Schirmerreschaft der Deutschen Gesellschaft for Nukelarmedizin.]" (Summary in English is provided on page 42); *Nuklearmedizin,* 35(2):42–52; Date of Publication: Apr. 1996; Place of Publication: Germany.

(List continued on next page.)

*Primary Examiner*—David V Bruce
(74) *Attorney, Agent, or Firm*—Hoffmann & Baron, LLP; Irving N. Feit

(57) ABSTRACT

A three dimensional mask of the lungs can be automatically created by thresholding, labeling connected components, selecting the dominant object, and alternately employing dilation and erosion operations. With this mask the lungs can be separated from the other anatomic structures on volumetric CT images. Local density maxima in the lungs are then determined by sequentially decreasing thresholds. As the threshold declines, more and more objects (a 3D object is a group of connected voxels with density values larger than the threshold) become apparent. Geometrically overlapped objects at the subsequent threshold levels are either merged into one object or identified as local density maximum (maxima) and plateau. This process terminates if the threshold reaches a predefined density value. Other information about small lung nodules such as compact shape and size are combined into the algorithm to further remove those detected local density maxima that are not likely to be nodules.

15 Claims, 14 Drawing Sheets

OTHER PUBLICATIONS

Author: M. D. Seemann, T. Beinert, F. Spelsberg, B. Obst, H. Dienemann, U. Fink, P. Kohz, and M. Reiser; Title: "Differentiation of solitary pulmonary coin lesions by high–resolution computerized tomography" (Summary in English provided on page 580); *Radiology,* 36(7):579–585; Date of Publication: Jul. 1996; Place of Publication: Germany.

Author: J. Serra; *Image analysis and mathematical morphology.;* pp. 34–92; Academic Press, London; Date of Publication: 1982; Place of Publication: London.

Author: J. Serra; Title: "Introduction to Morphological Filters"; *Image analysis and mathematical morphology; Volume 2: Theoretical advances,* pp. 101–114; Academic Press, London; Date of Publication: 1988; Place of Publication: London.

Author: S. W. Tamarkim; Title: "Spiral computed tomography and computed tomographic angiography"; In J. R. Haaga, C. F. Lanzieri, D. J. Sartoris, and E. A. Zehrouni, editors, *Computed tomography and magnetic resonance imaging of the whole body.* Mosby; pp. 1694–1706; Date of Publication: 1994; Place of Publication: U.S.

Author: W. Press; Title: "Numerical Recipes in C"; $2^{nd}$ Edition, Cambridge University Press; pp. 402–420; Date of Publication: 1992; Place of Publication: unknown.

Author: M.S. Brown, M.F. McNitt–Gray, J.G. Goldin and D.R. Aberle; Title: "Model–based segmentation architecture for lung nodule detection in CT"; RSNA 2000 annual meeting.

Author: S.G. Erberich. K.S. Song, H. Arakawa, H.K. Huang, R. Webb, K.S. Hoo, B.W. Loo; Title: "Knowledge–based lung nodule detection from helical CT" (Text of Publication only as Figures are not available); *RSNA 1997 annual meeting.*

Author: K. Kanazawa, M. Kubo, N. Niki, H. Satoh, H. Ohmatsu, K. Eguchi, N. Moriyama; Title: "Computer Assisted Diagnosis of Lung Cancer Using Helical X–ray CT"; *Proceeings of ICPR,* pp. 381–385; Date of Publication: 1996; Place of Publication: U.S.

Author: N. Otsu; Title: "A threshold selection method from gray–level histograms"; IEEE Trans. Systems Man Cybernet, 9(1), pp. 62–66; Date of Publication: 1979; Place of Publication: Japan.

Author: C.L. Novak, D.P. Naidich, L. Fan, J. Qian, J.P. Ko, A.N. Rubinowitz; Title: "Improving Radiologists' Confidence of Interpreting Low–dose Multidetector Lung CT Screening Studies Using an Interactive CAD system"; Scientific paper presentation, RSNA $87^{th}$ scientific assembly and annual meeting, Nov. 25–30, 2001.

Author: S. G. Armato, III, F. Li, M.L. Giger; Title: "Performance of Automated CT Lung Nodule Detection on Missed Cancers"; scientific paper presentation, RSNA $87^{th}$ scientific assembly and annual meeting, Nov. 25–30, 2001.

Author: M.K. Gurcan, N. Petrick, B. Sahiner, H.P. Chan, P.N. Cascade, E.A. Kazerooni, L.M. Hadjiiski; Title: "Computerized lung nodule detection on thoracic CT images; combined rule–based and statistical classifier for false positive reduction"; *SPIE,* vol. 4322, pp. 686–692; Date of Publication: 2001; Place of Publication: U.S.

Author: O. Karacan, O.A. Ibis, S. Akcay, O. Akkoca, F.O. Eyuboglu, and M. Coskun: Title: "Chest readiography and the solitary pulmonary nodule"; *Journal of Radiology;* Date of Publication: 2002; Place of Publication: unknown.

Author: G. Cittadini Jr., R. Conzi, and G. Motta; Title: "Spiral computed tomography in the diagnosis and staging of bronchopulmonary carcinoma"; *Chir Ital,* 47(3):13–17; Date of Publication: 1995; Place of Publication: U.S.

Author: ACR–NEMA Standards Committee. *Digital Imaging and Communications in Medicine* (*DICOM*): *Version 3.2.* Rosslyn, VA; Date of Publication: 1999; Place of Publication: U.S.

Author: R. C. Gonzales and R. E. Woods; *Digital Image Processing.* Addison–Wesley, Reading, MA; Date of Publication: 1992; Place of Publication: U.S.

Author: R. Jain, R. Kasturi, and B. G. Schunck. *Machine Vision.* McGraw–Hill, New York; Date of Publications: 1995; Place of Publication: U.S.

Author: A. P. Reeves. W. J. Kostis, C. 1. Henschke, B. Zhao, and D.F. Yankelevita; Title: "Three–dimensional feature characterization of small pulmonary nodules from helical CT images"; *Radiology,* 209P:163, Date of Publication: Nov. 1998; Place of Publication: U.S.

Author: J. Remy, M. Remy–Jardin. F. Giraud, and J. Wannebroucq; Title: "Spiral volumetric scanning and its applications in thoracic pathology"; *Rev Mal Respir,* 11(1):13–27; Date of Publication: 1994; Place of Publication: U.S.

Author: S. Sasaoka. H. Takabatake, M. Mori, H. Natori, and S. Abe; Title: "Digital analysis of pulmonary nodules–potential usefulness of computer–aided diagnosis for differentiation of benign from malignant nodules"; *Nippon Kyobu Shikkan Gakkai Zasshi,* 33(5):489–496, Date of Publication: May 1995; Place of Publication: U.S.

Author: P. Chandrascekhar, L. Wolff, E. Zerhouni, and W. Mitzner; Title: "Segmentation of 3 pulmonary trees using mathematical morphology"; In P. Maragos, R. W. Schafer, and M. A. Butt, editors, *Mathematical Morphology and its Applications to Image and Signal Processing,* pp. 409–416. Kluwer Academic Press; Date of Publication: May 1996; Place of Publication: U.S.

Author: D. F. Yankelevitz, A. P. Reeves, W. J. Kostis, B. Zhao, and C. I. Henschke: Title: "Determination of malignancy in small pulmonary nodules based on volumetrically determined growth rates"; *Radiology,* 209P:375; Date of Publication: Nov. 1998; Place of Publications: U.S.

Author: S. Hu, E. A. Hoffman, and J.M. Reinhardt; Title: "Automatic Lung Segmentation for Accurate Quantitation of Volumetric X–Ray CT Images"; *IEEE Transactions on Medical Imaging,* vol. 20, No. 6; Date of Publication: Jun. 2001; Place of Publication:.

Author: J. Hsieh; Title: "Generalized Adaptive Median Filters and their Application in Computed Tomography"; *SPIE,* vol. 2298, pp. 662–669, Date of Publication: 1994; Place of Publication: U.S.

Author: Y. Lee, T., Hara, H. Fujita, S. Itoh, and T. Ishigaki; Title: "Automatic Detection of Pulmonary Nodules in Helical CT Images Based on an Improved Template–Matching Technique"; *IEEE Transactions on Medical Imaging,* vol. 20, No. 7, pgs. 595–604; Date of Publication: Jul 2001; Place of Publication:.

Author: F. Maes, A. Collignon, D. Vandermeulen, G. Marchal and P. Suetens: Title: "Multimodality image registration by maximization of mutual information"; *IEEE Transactions on Medical Imaging,* vol. 16, No. 2, pgs. 187–198: Date of Publication: Apr. 1997; Place of Publication:.

Author: Takagi, N.; Kawata, Y., Nikvi, N.; Morit, K.; Ohmatsu, H.; Kakinuma, R.; Eguchi, K.; Kusumoto, M.; Kaneko, M.; Mriyama, N.; Title: "Computerized characterization of contrast enhancement patterns for classifying pulmonary nodules"; *Image Processing, 2000. Proceedings. 2000 International Conference* on vol. 1, pp. 188–191; Date of Publication: 2000; Place of Publication:.

Author: A. P. Reeves, W. J. Kostis; Title: "Computer–Aided Diagnosis of Small Pulmonary Nodules"; *Seminars in Ultrasound, CT. and MRI,* vol. 21, No. 2, pgs. 116–128; Date of Publication: Apr. 2000; Place of Publication:

Author: W. J. Kostis, A. P. Reeves, D. F. Yankelevitz, C.I. Henschke; Title: "Three–dimensional segmentation of solitary pulmonary nodules from helical CT scans"; CARS '99 *Computer Assisted Radiology and Surgery; Proceedings of the 13$^{th}$ International Congress and Exhibition,* pgs. 203–207; Date of Publication: 1999; Place of Publication:.

Author: Li Fan, Carol L. Novak, Jiangzhong Qian, Gerhard Kohl, and David P. Naidich; Title: "Automatic Detection of Lung Nodules from Multi–Slice Low Dose CT Images"; Proc SPIE 2001; 4322–1828–1835; Date of Publication: 2001; Place of Publication: U.S.

Author: Binsheng Zhao, Anthony Reeves, David Yankelevitz, and Claudia Henschke; Title: "Three–Dimensional multi–criterion automatic segmentation of pulmonary nodules of helical CT images"; Optical Engineering, 38(8):1340–1347; Date of Publication: 1999; Place of Publication:.

Author: American Cancer Society; Title: "Cancer Facts & Figures 2002"; 1599 Clifton Road, NE, Atlanta, GA, 30329–4251.

Author: Claudia I. Henschke, D.P. Naidich, D.F. Yankelevitz, G. McGuinness, D.I. McCauley, J.P. Smith, D.M. Libby, M.W. Pasmantier, M. Vazquez, J. Koizumi, D. Flleder, N.K. Altorki, and O.S. Miettinen; Title: "Early Lung Cancer Action Project: Initial Findings on Repeat Screening"; Cancer Jul. 1, 2001; 92(1):153–159; Date of Publication: Jul. 1, 2001; Place of Publication:.

Author: S.G. Armato III, M.L. Giger, J.T. Blackburn, K. Doi, H. MacMahon; Title: "Three–dimensional approach to lung nodule detection in helical CT"; *SPIE,* vol. 3661, pp. 553–559; Date of Publication: 1999; Place of Publication: U.S.

Author: S.L. Lou, C.L. Chang, K.P. Lin and T. Chen; Title: "Object based deformation technique for 3–D CT lung nodule detection"; *SPIE,* vol. 3661, pp. 1544–1552; Date of Publication: 1999; Place of Publication: U.S.

Author: T. Okumura, T. Miwa, Jun–ichi Kako, S. Yamamoto, M. Matsumoto, Y. Tateno, T. Linua and T. Matsumoto: Title: "Image processing for computer–aided diagnosis of lung cancer screening system by CT (LSCT)"; *SPIE,* vol. 3338, pp. 1314–1322; Date of Publication: 1998, Place of Publication: U.S.

Author: M. Fiebich, C. Weitholt, B.C. Render, S.G. Armato, K.R. Hoffmann, D. Wormanns and S. Diederich; Title: "Automatic detection of pulmonary nodules in low–dose screening thoracic CT examinations"; *SPIE,* vol. 3661, pp. 1434–1439; Date of Publication: 1999; Place of Publication: U.S.

Author: H. Taguchi, Y. Kawata and N. Niki, H. Satoh, H. Ohmatsu, K. Eguchi, M. Kaneko and N. Moriyama; Title: "Lung cancer detection based on helical CT images using curved surface morphology analysis"; *SPIE,* vol. 3661, pp. 1307–1313; Date of Publication: 1999; Place of Publication: U.S.

Author: S–C B. Lo, S–L A. Lou, J–S Lin, M.T. Freedman, M.V. Chien and S.K. Mun; Title: "Artificial convolution neural Network techniques and applications for lung nodule detection"; *IEEE transactions on medical imaging,* vol. 14, No. 4, pp. 711–718; Date of Publication: 1995; Place of Publication:

Author: W.J. Kostis; Title: "Three–dimensional computed tomographic image analysis for early cancer diagnosis in small pulmonary nodules"; Ph.D. dissertation, Cornell University; Date of Publication: 2001; Place of Publication: U.S.

Author: R. Kakinuma, H. Ohmatsu, M. Kaneko, K. Eguchi, K. Naruke, K. Nagai; Title: "Detection failures in spiral CT screening for lung cancer: analysis of CT findings"; Radiology 212, pp. 61–66; Date of Publication: 1999; Place of Publication:.

Author: F. Li, S. Sone, H. Abe, H.M. MacMahon, S.G. Armato, K. Doi; Title: "Missed Lung Cancers in low–dose Helical CT Screening Obtained from a General Population"; scientific paper presentation, RSNA 87$^{th}$ scientific assembly and annual meeting, No. 25–30, 2001.

Author: M. Remy Jardin, F. Giraud, C–H Marquette; Title: "Pulmonary nodules: detection with thick section spiral CT versus conventional CT"; Radiology, 187(No. 2), pp. 513–520; Date of Publication: 1993; Place of Publication:.

Author: J.A. Buckley, W. W. Scott. S.S. Siegelman, et al.; Title: "Pulmonary nodules: effect of increased data sampling on detection with spiral CT and confidence in diagnosis"; Radiology, 196, pp. 395–400; Date of Publication: 1995; Place of Publication:.

Author: Y. Kawata, N. Niki, H. Ohmatsu, M. Kusumoto, R. Kakinuma, K. Mori, N. Nishiyama, K. Eguchi, M. Kaneko and N. Moriyama: Title: "Tracking interval changes of pulmonary nodules using a sequence of three–dimensional thoracic images"; *In Medical Imaging 2000: Image Processing. Proceedings of SPIE,* vol. 3979, pp. 86–96; Date of Publication: 2000; Place of Publication: U.S.

Author: Y. Kawata, N. Niki, H. Ohmatsu, M. Kusumoto, R. Kakinuma, K. Mori, N. Nishiyama, K. Eguchi, M. Kaneko, and N. Moriyama; Title: "Analysis of evolving processes in pulmonary nodules using a sequence of three–dimensional thoracic images"; In M. Sonka d K.M. Hanson, editors, *Medical Imaging 2001: Image Processing, Proceedings of SPIE,* vol. 4322, pp. 1890–1901; Date of Publication: 2001; Place of Publication: U.S.

Author: A. Akanuma: Title: "Clinical method to estimate time of origin and maximum volume of malignant tumors"; *Radiation Medicine,* 1(1):89–104; Date of Publication: Jan.–Mar. 1983; Place of Publication: Japan.

Author: E. Arana, P. Delicado, and L. Marti–Bonmati.; Title: "Validation procedures in radiologic diagnositc models"; Neural network and logistic regression. *Investigative Radiology,* 34(10):636–642; Date of Publication: Oct. 1999; Place of Publication: Spain.

Author: S. G. Armato, III, M. L. Giger, K. Ashizawa, and H. MacMahon; Title: "Automated lung segmentation in digital lateral chest radiographs"; *Medical Physics,* 25(8):1507–1520, Date of Publication: Aug. 1998; Place of Publication: U.S.

Author: S. G. Armato, III, M. L. Giger, C. J. Morgan, J. T. Blackburn, K. Doi, and H. MacMahon: Title: "Computerized detection of pulmonary nodules on CT scans"; *Radiographics,* 19(5):1303–1311; Date of Publication: Sep.–Oct. 1999; Place of Publication: U.S.

Author: P. J. Besle and R. C. Jain; Title: "Invariant surface characteristics for 3D object recognition in range images"; *Computer Vision, Graphics, and Image processing,* 33(1):33–80; Date of Publication: Jan. 1986; Place of Publication: U.S.

Author: R. N. Bracewell and S. J. Wernecke: Title: "Image reconstruction over a finite field of view"; *Journal of the Optical Society of America,* 65:1342–1346; Date of Publication: 1975; Place of Publication: U.S.

Author: M. S. Brown, M. F. McNitt–Gray, N. J. Mankovich, J. G. Goldin, J. Hiller, L. S. Wilson, and D. R. Aberle; Title: "Method for segmenting chest CT image data using an anatomical model; Preliminary results"; *IEEE Transactions on Medical Imaging,* 16(6):828–839; Date of Publication: Dec. 1997; Place of Publication: U.S.

Author: M. J. Carreira, D. Cabello, M. G. Penedo, and A. Mosquera; Title: "Computer–aided diagnoses: Automatic detection of lung nodules"; *Medical Physics,* 25(10):1998–2006; Date of Publication: Oct. 1998; Place of Publication: Spain.

Author: J. Collins and E. J. Stern: Title: "Ground–glass opacity of CT: the ABCs"; *AJR American Journal of Roentgenology,* 169(2):355–367; Date of Publication: Aug. 1997; Place of Publication: U.S.

Author: V. P. Collins, R. K. Loeffler, and H. Tivey; Title: "Observations on growth rates of human tumors"; *American Journal of Roentgenology,* 76:988–1000; Date of Publication: 1956; Place of Publication: U.S.

Author: A. M. Cormack.; Title: "Representation of a function by its line integrals with some radiological applications"; *Journal of Applied Physics,* 34:2722–2727; Date of Publication: 1963; Place of Publication: U.S.

Author: A.M. Cormack.; Title: "Representation of a function by its line integrals with some radiological applications II"; *Journal of Applied* Physics, 34:2908–2913; Date of Publication: 1964; Place of Publication: U.S.

Author: P. Croisille, M. Souto, M. Cova, S. Wood, Y. Afework, J. E. Kuhlman, and E. A. Zerhouni; Title: "Pulmonary nodules: Improved detection with vascular segmentation and extraction with spiral CT"; Work in progress. *Radiology* 197(2):397–401; Date of Publication: Nov. 1995; Place of Publication: U.S.

Author: S. Dholakia and D. C. Rappaport: Title: "The solitary pulmonary nodule. Is it malignant or benign?"; *Postgraduate Medicine,* 99(2):246–250; Date of Publication: Feb. 1996; Place of Publication: U.S.

Author: C. E. Engeler, J. H. Tashjian, S. W. Trenkner, and J. W. Walsh; Title: "Ground–glass opacity of the lung parenchyma: a guide to analysis with high–resolution CT"; *AJR American Journal of Roentgenology,* 160(2):249–251; Date of Publication: Feb. 1993; Place of Publication: U.S.

Author: B. J. Flehinger. M. Kimmel, T. Polyak, and M. R. Melamed; Title: "Screening for lung cancer"; The Mayo Lung Project revisited. *Cancer,* 72(5):1573–1580; Date of Publication: Sep. 1, 1993; Place of Publication: U.S.

Author: R. S. Fontana, D. R. Sanderson, L. B. Woolner, W.F. Taylor, W. E. Miller, J. R. Muhm, P. E. Bernatz, W. S Payne, P. C. Pairolero, and E. J. Bergstralh; Title: "Screening for lung cancer"; A critique of the Mayo Lung Project, *Cancer* 67(4(suppl)):1155–1164; Date of Publication: Feb. 15 1991; Place of Publication: U.S.

Author: A. Van Gelder and J. Wilhems; Title: "Topological considerations in isosurface generation"; *ACM Transactions on Graphics,* 13(4):337–375; Date of Publication: Oct. 1994; Place of Publication: U.S.

Author: M. L. Giger, K. T. Bae, and H. MacMahon, Title: "Computerized detection of pulmonary nodules in computed tomography images"; *Investigative Radiology,* 29(4):459–465; Date of Publication: Apr. 1994; Place of Publication: U.S.

Author: M. L. Giger, K. Doi, and H. MacMahon: Title: "Image feature analysis and computer–aided diagnosis in digital radiography. 3. Automated detection of nodules in peripheral lung fields"; *Medical Physics,* 15(2):158–166; Date of Publication: Mar.–Apr. 1988; Place of Publication: U.S.

Author: J. W. Green and C. C. Lushbaugh; Title: "Histopathological study of the mode of inhibition of cellular proliferation by urethane", *Cancer Research,* 9:199–209; Date of Publication: 1949; Place of Publication: U.S.

Author: Gurney, Jud W.; Title: "Determining the likelihood of malignancy in solitary pulmonary nodules with Bayesian analysis"; Part 1. Theory. *Radiology,* 186(2):405–413; Date of Publication: Feb. 1993; Place of Publication: U.S.

Author: J. A. Hanley and B. J. McNeil: Title: "The meaning and use of the area under a receiver operating characteristic (ROC) curve"; *Radiology,* 143(1):29–36; Date of Publication: Apr. 1982; Place of Publication: Canada.

Author: C.I. Henschke, D.I. McCauley, D.F. Yankelevitz, D. P. Naidich, G. McGuinness, O. S. Miettinen, D. M. Libby, M. W. Pasmantier, J. Koizumi, N. K. Altorki, and J. P. Smith; Title: "Early Lung Cacer Action Project: overall design and findings from baseline screening;" *Lancet,* 354(9173):99–105; Date of Publication: Jul. 1999; Place of Publication: U.S.

Author: C. J. Herold, A. A. Bankier, and D. Fleischmann; Title: "Lung metastases"; *European Radiology,* 6(5):596–606; Date of Publication: 1996; Place of Publication: Austria.

Author: G. N. Hounsfield; Title: "Computerized transverse axial scanning (tomography). I. Description of system"; *British Journal of Radiology,* 46(552):1016–1022; Date of Publication: Dec. 1973; Place of Publication: England.

Author: G. N. Hounsfield; Title: "Computed medical imaging"; Nobel lecture, Dec. 8, 1979, *Journal of Computer Assisted Tomography,* 4(5):665–674; Date of Publication: Oct. 1980; Place of Publication: England.

Author: Z. Huo, M. L. Giger, C. J. Vyborny, U. Bick, P. Lu, D. E. Wolverton, and R. A. Schmidt; Title: "Analysis of spiculation in the computerized classification of mammographic masses"; *Medical Physics,* 22(10):1569–1579; Date of Publication: Oct. 1995; Place of Publication: U.S.

Author: Z. Huo, M. L. Giger, C. J. Vyborny, D. E. Wolverton, R. A. Schmidt, and K. Doi; Title: "Automated computerized classification of malignant and benign masses on digitized mammograms"; *Academic Radiology,* 5(3):155–168; Date of Publication: Mar. 1998; Place of Publication: U.S.

Author: S. Itoh, M. Ikeda, T. Isomura, T. Endo, K. Yamakawa, K. Itoh, S. Naganawa, K. Maruyama, and T. Ishigaki; Title: "Screening helical CT for mass creening of lung cancer: application of low–dose and single–breath–hold scanning"; *Radiation Medicine,* 16(2):75–83; Date of Publication: Mar.–Apr. 1998; Place of Publication: Japan.

Author: L. R. Kaiser and J. B. Shrager; Title: "Video–assisted thoracic surgery: the current state of the art"; *AJR American Journal of Roentgenology,* 99(2):246–250; Date of Publication: Feb. 1996; Place of Publication: U.S.

Author: W. A. Kalender: Title: "Technical foundations of spiral CT"; *Seminars in Ultrasound, CT, and MRI,* 15(2):81–89; Date of Publication: Apr. 1994; Place of Publication: Germany.

Author: W. A. Kalender; "Thin–section three–dimensional spiral CT: is isotropic imaging possible?"; *Radiology,* 197(3):578–580; Date of Publication: Dec. 1995; Place of Publication: Germany.

Author: W. A. Kalender, W. A. Seissle, E. Klotz, and P. Vock: Title: "Spiral volumetric CT with single breath–hold technique continuous transport and continuous scanner rotation"; *Radiology,* 176(1):181–183; Date of Publication: Jul. 1990; Place of Publication: Switzerland.

Author: M. Kaneko, K. Eguchi, H. Ohmatsu, R. Kakinuma, T. Naruke, K. Seumasu, and N. Moriyama: Title: "Peripheral lung cancer: screening and detection with low–dose spiral CT versus radiography"; *Radiology,* 201(3):798–802; Date of Publication: Dec. 1996; Place of Publication: Japan.

Author: Y. Kawata, N. Niki, H. Ohmatsu, K. Eguchi, and N. Moriyama; Title: "Shape analysis of pulmonary nodules based on this section CT images"; *SPIE Proceedings,* 3034:964–974; Date of Publication: Feb. 1997; Place of Publication: Japan.

Author: J. H. Kim, J. G. Im, M. C. Han, B. G. Min, and C. W. Lee; Title: "Improved visualization of simulated nodules by adaptive enhancement of digital chest radiography"; *Academic Radiology,* 1(2):93–99; Date of Publication: Oct. 1994: Place of Publication: South Korea.

Author: T. Kobayashi, X.–W. Xu, H. MacMahon, C. E. Metz, and K. Doi; Title: "Effect of a computer–aided diagnosis scheme on radiologists' performance in detection of lung nodules on radiographs"; *Radiology,* 199(3):843–848; Date of Publication: Jun. 1996; Place of Publication: U.S.

Author: A. K. Laird; Title: "Dynamics of tumor growth: Comparison of growth rates and extrapolation of growth curve to one cell"; *British Journal of Cancer,* 19:278–291; Date of Publication: 1965; Place of Publication: U.S.

Author: S. H. Landis, T. Murray, S. Bolden, and P. A. Wingo; Title: "Cancer statistics, 1999"; *CA: A Cancer Journal for Clinicians,* 49(1):8–31, Date of Publication: Jan.–Feb. 1999; Place of Publication: U.S.

Author: G. A. Lillington: Title: "Management of solitary pulmonary nodules"; *Postgraduate Medicine,* 101(3):145–150, Date of Publication: Mar. 1997; Place of Publication: U.S.

Author: W. E. Lorensen and H. E. Cline; Title: "Marching cubes: A high resolution 3D surface construction algorithm"; *Computer Graphics,* 21(4):163–169; Date of Publication: Jul. 1987; Place of Publication: U.S.

Author: F. Mao, W. Qian, J. Gaviria, and L. P. Clarke: Title: "Fragmentary window filtering for multiscale lung nodule detection: Preliminary study"; *Academic Radiology,* 5(4):306–311, Date of Publication: Apr. 1998; Place of Publication: U.S.

Author: T. Matsumoto, H. Yoshimura, K. Doi, M. L. Giger, A. Kano, H. MacMahon, K. Abe, and S. M. Montner; Title: "Image feature analysis of false–positive diagnoses produced by automated detection of lung nodules"; *Investigative Radiology,* 27(8):587–597, Date of Publication: Aug. 1992; Place of Publication: U.S.

Author: M. F. McNitt–Gray, E. M. Hart, N. Wyckoff, J. W. Sayre, J. G. Goldin, and D. R. Aberle; Title: "A pattern classification approach to characterizing solitary pulmonary nodules imaged on high resolution CT: Preliminary results"; *Medical Physics,* 26(6):880–888; Date of Publication: Jun. 1999; Place of Publication: U.S.

Author: M.R. Melamed, B. J. Flehinger, M. B. Zaman, R. T. Heelan, W. A. Perchick, and N. Martini; Title: "Screening for early lung cancer. Results of the Memorial Sloan–Kettering study in New York"; *Chest,* 86(1):44–53, Date of Publication: Jul. 1984; Place of Publication: U.S.

Author: S. Mitruka, R. J. Landreneau, M. J. Mack, L. S. Fetterman, J. Gammie, S. Bartley, S. R. Sutherland, C. M. Bowers, R. U. Keenan RJ, P. F. Ferson, and R. J. Weyant: Title: "Diagnosing the indeterminate pulmonary nodule: percutaneous biopsy versus thoracoscopy"; *Surgery,* 118(4):676–684; Date of Publication: Oct. 1995; Place of Publication: U.S.

Author: O. Monga, R. Deriche, and J.–M. Rocchisani; Title: "3D edge detection using recursive filtering: Application to scanner images"; *Computer Vision, Graphics, and Image Processing: Image Understanding,* 53(1):76–87; Date of Publication: Jan. 1991; Place of Publication: France.

Author: H. Nathan; Title: "Management of solitary pulmonary nodules. An organized approach based on growth rate and statistics"; *JAMA,* 227(10):1141–1144, Date of Publication: Mar. 1974; Place of Publication: U.S.

Author: M. H. Nathan, V. P. Collins, and R. A. Adams; Title: "Differentiation of benign and malignant pulmonary nodules by growth rate"; *Radiology,* 79:221–231; Date of Publication: 1962; Place of Publication: U.S.

Author: R. Pearl and L. J. Reed; Title: "On the rate of growth of the population of the United States since 1790 and its mathematical presentation"; *Proceedings of the National Academy of Sciences,* 6:275–285; Date of Publication: 1920; Place of Publication: U.S.

Author: J. Peiss, M. Verlande, W. Ameling, and R. W. Guenther; Title: "Classification of lung tumors on chest radiographs by fractal texture analysis"; *Investigative Radiology,* 31(10):625–629; Date of Publication: Oct. 1996; Place of Publication: Germany.

Author: M. G. Penedo, M. J. Carreira, A. Mosquera, and D. Cabello: Title: "Computer–aided diagnosis: A neural–network–base approach to lung nodule detection", *IEEE Transactions on Medical Imaging,* 17(6): 872–880; Date of Publication: Dec. 1998; Place of Publication: Spain.

Author: R. J. Prokop and A. P. Reeves; Title: "A survey of moment–based techniques for unoccluded object representation and recognition"; *CVGIP: Graphical Models and Image Processing,* 54(5):438–360; Date of Publication: Sep. 1992; Place of Publication: U.S.

Author: R. D. Pugatch; Title: "Radiologic evaluation in chest malignancies. A review of imaging modalities"; *Chest,* 107(6 (suppl.)):294S–297S; Date Publication: Jun. 1995; Place of Publication: U.S.

Author: A. P. Reeves, W. J. Kostis, D. F. Yankelevitz, and C. I. Henschke; Title: "Three–dimensional shape characterization of solitary pulmonary nodules from helical CT scans"; In H. U. Lemke, M. W. Vannier, K. Inamura, and A. G. Farman, editors, *Proceedings, of Computer Assisted Radiology and Surgery* (*CARS '99*), pp. 83–87. Elsevier Science; Date of Publication: Jun. 1999; Place of Publication: U.S.

Author: A. P. Reeves, R. J. Prokop, S. E. Andrews, and F. P. Kuhl; Title: "Three–dimensional shape analysis using moments and Fourier descriptors"; *IEEE Transactions on Pattern Analysis and Machine Intelligence,* 10(6):937–943; Date of Publication: Nov. 1988; Place of Publication: U.S.

Author: A. P. Reeves and B. S. Wittner; Title: "Shape analysis of three dimensional objects using the method of moments"; in *Proceedings of 1983 IEEE Conference on Computer Vision and Patten Recognition,* pp. 20–26; Date of Publication: Jun. 1983; Place of Publication: U.S.

Author: T. W. Ridler and S. Calvard; Title: "Picture thresholding using an iterative selection method"; *IEEE Transactions on Systems, Man, and Cybernetics, SMC*–8(8):630–632; Date of Publication: Aug. 1978; Place of Publication: London.

Author: K. V. Rolston, S. Rodriguez, M. Dholakia, E. Whimbey E, and I. Raad; Title: "Pulmonary infections mimicking cancer: a retrospective; three–year review"; *Support Care Cancer,* 5(2):90–93; Date of Publication: Mar. 1997; Place of Publication: U.S.

Author: S. Sanada, K. Doi, and H. MacMahon; Title: "Image feature analysis and computer–aided diagnosis in digital radiography: automated delineation of posterior ribs in chest images"; *Medical Physics,* 18(5):964–971; Date of Publication: Sep.–Oct. 1991; Place of Publication: U.S.

Author: M. D. Seemann, A. Staebler, T. Beinert, H. Dienemann, B. Obst, M. Matzko, C. Pistitsch, and M. F. Reiser; Title: "Usefulness of morphological characteristics for the differentiation of benign from malignant solitary pulmonary lesions using HRCT;" *European Radiology,* 9(3):409–417; Date of Publication: 1999; Place of Publication: Germany.

Author: R., Shah, S. Sabanathan, J. Richardson, A. J. Mearns, and C. Goulden; Title "Results of surgical treatment of stage I and II lung cancer"; *Journal of Cardiovascular Surgery,* 37(2):169–172; Date of Publication: Apr. 1996; Place of Publication: United Kingdom.

Author: R. H. Sherrier, C. Chiles, W. E. Wilkinson, G. A. Johnson, and C. E. Ravin; Title: "Effects of image processing on nodule detection rates in digitized chest radiographs: ROC study of observer performance"; *Radiology,* 166(2):447–450; Date of Publication: Feb. 1998; Place of Publication: U.S.

Author: S. Sone, S. Takashima, F. Li, Z. Yang, T. Honda, Y. Maruyama, M. Hasegawa, T. Yamanda, K. Kubo, K. Hanamura, and K. Asakura; Title: "Mass screening for lung cancer with mobile spiral computed tomography scanner"; *Lancet,* 351 (9111);1242–1245; Date of Publication: Apr. 1998; Place of Publication: Japan.

Author: M. Sonak, G. Sundararmoorthy, and E. A. Hoffman: Title: "Knowledge–based segmentation of intrathoracic airways from multidimensional high resolution CT images"; . *SPIE,* 2168:73–85; Date of Publication: Aug. 1994; Place of Publication: U.S.

Author: J. S. Spratt, J. S. Meyer, and J. A. Spratt; Title: "Rates of growth of human solid neoplasms: Part I"; *Journal of Surgical Oncology,* 60(2):137–146; Date of Publication: Oct. 1995; Place of Publication: U.S.

Author: S. J. Swensen, J. R. Jett, W. S. Payne, R. W. Viggiano, P. C. Pairolero, and V. F. Trastek; Title: "An integrated approach to evaluation of the solitary pulmonary nodule"; *Mayo Clinic Proceedings,* 65(2):173–186; Date of Publication: Feb. 1990; Place of Publication: U.S.

Author: S. J. Swensen, M. D. Silverstein, D. M. Ilstrup, C. D. Schleck, and E. S. Edell; Title: "The probability of malignancy in solitary pulmonary nodules. Application to small radiologically indeterminate nodules"; *Archives of Internal Medicine,* 157(8):849–855; Date of Publication: Apr. 1997; Place of Publication: U.S.

Author: S. Toshioka, K. Kanazawa, N. Niki, H. Satoh, H. Ohmatsu, K. Eguchi, and N. Moriyama; Title: "Computer aided diagnosis system for lung cancer based on helical CT images"; *SPIE Proceedings,* 3034:975–984; Date of Publication: Feb. 1997; Place of Publication: Japan.

Author: J. D. Urschel; Title: "Surgical treatment of peripheral small cell lung cancer"; *Chest Surg Clin N Am,* 7(1):95–103; Date of Publication: Feb. 1997; Place of Publication: U.S.

Author: K. Usuda, Y. Saito, M. Sagawa, M. Sato, K. Kanma, S. Takahashi, C. Endo, Y. Chen. A. Sakurada, and S. Fujimura; Title: "Tumor doubling time and prognostic assessment of patients with primary lung cancer"; *Cancer,* 74(8):2239–2244, Date of Publication: Oct. 1994; Place of Publication: Japan.

Author: N. F. Vittitoe, J. A. Baker, and C. E. Floyd; Title: "Fractal texture analysis in computer–aided diagnosis of solitary pulmonary nodules"; *Academic Radiology,* 4(2):96–101; Date of Publication: Feb. 1997; Place of Publication: U.S.

Author: P. Vock, M. Soucek, M. Daepp, and W. A. Kalender; Title: "Lung: spiral volumetric CT with single–breath–hold technique"; *Radiology,* 176(3):864–867; Date of Publication: Sep. 1990; Place of Publication: Switzerland.

Author: W. Weiss; Title: "Implications of tumor growth rate for the natural history of lung cancer"; *Journal of Occupational Medicine,* 26(5):345–352; Date of Publication: May 1984; Place of Publication: U.S.

Author: S. A. Wood, E. A. Zerhouni, J. D. Hoford, E. A. Hoffman, and W. Mitzner; Title: "Measurement of tree–dimensional lung tree structures by using computed tomography"; *Journal of Applied Physiology,* 79(5):1687–97; Date of Publication: Nov. 1995: Place of Publication: U.S.

Author: X.–W. Xu and K. Doi; Title: "Image feature analysis for computer–aided diagnosis: Accurate determination of ribcage boundary in chest radiographs"; *Medical Physics,* 22(5):617–626; Date of Publication: May 1995; Place of Publication: U.S.

Author: X.–W. Xu and K. Doi; Title: Image feature analysis for computer–aided diagnosis: Detection of right and left hemidiaphragm edges and delineation of lung field in chest radiographs; *Medical Physics,* 23(9):1613–1624; Date of Publication: Sep. 1996; Place of Publication: U.S.

Author: X.–W. Xu, K. Doi, T. Kobayashi, H. MacMahon, and M. L. Giger; Title: "Development of an improved CAD scheme for automated detection of lung nodules in digital chest images"; *Medical Physics,* 24(9):1395–1403; Date of Publication: Sep. 1997; Place of Publication: U.S.

Author: S. Yamamoto, I. Tanaka, M. Senda, Y. Tateno, T. Linuma, T. Matsumoto, and M. Matsumoto: Title: "Image processing for computer–aided diagnosis of lung cancer by CT (LSCT)"; *Systems and Computers in Japan,* 25(2):67–80; Date of Publication: Feb. 1994; Place of Publication: Japan.

Author: D. F. Yankelevitz, C. I. Henschke, J. H. Koizumi, N. K. Altorki, and D. Libby: Title: "CT–guided transthoracic needle biopsy of small solitary pulmonary nodules"; *Clinical Imaging,* 21(2):107–10; Date of Publication: Mar.–Apr. 1997; Place of Publication: U.S.

Author: H. Yoshimura, M. L. Giger, K. Doi, H. MacMahon, and S. M. Montner; Title: "Computerized scheme for the detection of pulmonary nodules: A nonlinear filtering technique"; *Investigative Radiology,* 27(2):124–129; Date of Publication: Feb. 1992: Place of Publication: U.S.

Author: T. Fleiter, E.M. Merkle, A.J. Aschoff, G. Lang, M. Stein, J. Gorich, F. Liewald, N. Rilinger, and R. Sokiranski; Title: "Comparison of real–time virtual and fiberoptic bronchoscopy in patients with bronchial carcinoma; opportunities and limitations"; *American Journal of Roentgenology,* 169(2):1591–1595; Date of Publication: Dec. 1997; Place of Publication: Germany.

Author: M. L. Giger, K.T. Bae, and H. MacMahon; Title: "Image processing and computer–aided diagnosis"; *Radiologic Clinics of North America,* 34(3):565–596, Date of Publication: May 1996; Place of Publication: U.S.

Author: P. A. Heng, P. F. Fung, T. T. Wong, Y. H. Siu, and H. Sun; Title: "Interactive navigation and bronchial tube tracking in virtual bronchoscopy"; *Studies in Health Technology and Informatics,* 62:130–133, Date of Publication: 1999; Place of Publication: Hong Kong.

Author: W. J. Kostis, A. P. Reeves, D. F. Yankelvitz, and C. I. Henschke; Title: "Three–dimensional segmentation of solitary pulmonary nodules from helical CT scans"; In H. U. Lemke, M. W. Vannier, K. Inamura, and A. G. Farman, editors, *Proceedings of Computer Assisted Radiology and Surgery* (*CARS'99*), pp. 203–207, Elsevier Science; Date of Publication: Jun. 1999; Place of Publication: U.S.

Author: F. Maes, A. Collingnon, D. Vandermeulen, G. Marchal, and P. Suetens. Title: "Multimodality image registration by maximization of mutual information"; *IEEE Transactions on Medical Imaging,* 16(2):187–198; Date of Publication: Apr. 1997; Place of Publication: Belgium.

Author: W. Park, E. A. Hoffman, and M. Sonka; Title: "Segmentation of intrathoracic airway trees: A fuzzy logic approach"; *IEEE Transactions on Medical Imaging,* 17(4):489–497; Date of Publication: Aug. 1998; Place of Publication: U.S.

Author: A. P. Reeves and W. J. Kostis; Title: "Computer–aided dignosis for lung cancer"; *Radiologic Clinics of North America,* 38(3):497–509; Date of Publication: May 2000; Place of Publication: U.S.

Author: R. M. Summers, D. H. Feng, S. M. Holland, M. C. Sneller, and J. H. Shelhamer; Title: "Virtual bronchoscopy: Segmentation method for real–time display"; *Radiology,* 200(3):857–862; Date of Publication: Sep. 1996; Place of Publication: U.S.

Author: J. K. Udupa; Title: "Three–dimensional visualization and analysis methodologies: a current perspective"; *Radiographics,* 19(3):783–806; Date of Publication: May–Jun. 1999; Place of Publication: U.S.

Author: W. M. Wells, III, P. Viola, H. Atsumi, S. Nakajima, and R. Kikinis; Title: "Multi–modal volume registration by maximization of mutual information"; *Medical Image Analysis,* 1(1):35–51; Date of Publication: Mar. 1996; Place of Publication: U.S.

Author: D. F. Yankelevitz, R. Gupta, B. Zhao, and C. I. Henschke;. Title: "Small pulmonary nodules: Evaluation with repeat CT–preliminary experience"; *Radiology,* 212(2):561–566; Date of Publication: Aug. 1999; Place of Publication: U.S.

Author: D. F. Yankelevitz, A. P. Reeves. W. J. Kostis, B. Zhao, and C. I. Henschke; Title: "Small Pulmonary Nodules: Volumetrically Determined Growth Rates Based on CT Evaluation"; Radiology, 217(1):251–256; Date of Publication: Oct. 2000; Place of Publication: U.S.

Author: A. P. Reeves and W. J. Kostis; Title: "Computer–Aided Diagnosis of Small Pulmonary Nodules"; *Seminars in Ultrasound, CT, and MRI,* 21(2):116–128; Date of Publication: Apr. 2000; Place of Publication: U.S.

Author: B. Zhao, W. J. Kostis, A. P. Reeves, D. F. Yankelevitz, and C. I. Henschke; Title: "Consistent Segmentation of Repeat CT Scans for Growth Assessment in Pulmonary Nodules"; Proceedings of the SPIE, Medical Imaging 1999; 3661:1012–1018; Date of Publication: May 1999; Place of Publication: U.S.

Author: S. Hu, E. A. Hoffman, and J.M. Reinhardt; Title: "Automatic Lung Segmentation for Accurate Quantitation of Volumetric X–Ray CT Images"; *IEEE Transactions on Medical Imaging,* vol. 20, No. 6; Date of Publication: Jun. 2001; Place of Publication: U.S.

Author: J. Hsieh; Title: "Generalized Adaptive Median Filters and their Application in Computed Tomography"; *SPIE,* vol. 2298, pp. 662–669, Date of Publication: 1994; Place of Publication: U.S.

Author: J. Hsieh; Title: "Adaptive Trimmed Mean Filter for CT Imaging"; Mathematical Methods in Medical Imaging III, Proceedings of *SPIE,* vol. 2299, pp. 316–324; Date of Publication: 1994; Place of Publication: U.S.

Author: H. Soltanian–Zadeh, J.P. Windham and J. Soltanianzadeh; Title: "CT Artifact Correction: An Image Processing Approach"; Medical Imaging 1996; Image Processing, Proceedings of SPIE, vol. 2710, pp. 477–485; Date of Publication: 1996; Place of Publication: U.S.

Author: A. P. Reeves, W. J. Kostis, D. F. Yankelevitz, C.I. Henschke; Title: "Analysis of Small Pulmonary Nodules without Explicit Segmentation of CT images"; *Radiological Society of North America—2000 Scientific Program,* vol. 217, pgs. 243–244; Date of Publciation: Nov. 2000; Place of Publication: U.S.

Author: Y. Lee, T., Hara, H. Fujita, S. Itoh, and T. Ishigaki; Title: "Automatic Detection of Pulmonary Nodules in Helical CT Images based on an Improved Template–Matching Technique"; *IEEE Transactions on Medical Imaging,* vol. 20, No. 7, pgs. 595–604; Date of Publication: Jul. 2001; Place of Publication: U.S.

Author: F. Maes, A. Collignon, D. Vandermeulen, G. Marchal and P. Suetens; Title: "Multimodality image registration by maximization of mutual information"; *IEEE Transactions on Medical Imaging,* vol. 16, No. 2, pgs. 187–198; Date of Publication: Apr. 1997; Place of Publication: U.S.

Author: Takagi, N.; Kawata, Y., Nikvi, N.; Morit, K.; Ohmatsu, H.; Kakinuma, R.; Eguchi, K.; Kusumoto, M.; Kaneko, M.; Moriyama, N.; Title: "Computerized characterization of contrast enhancement patterns for classifying pulmonary nodules"; *Image Processing, 2000. Proceedings. 2000 International Conference* on vol. 1, pp. 188–191; Date of Publication: 2000; Place of Publication: U.S.

Author: A. P. Reeves, W. J. Kostis; Title: "Computer–Aided Diagnosis of Small Pulmonary Nodules"; *Seminars in Ultrasound, CT. and MIR,* vol. 21, No. 2, pgs. 116–128; Date of Publication: Apr. 2000; Place of Publication: U.S.

Author: W. J. Kostis, A. P. Reeves, D. F. Yankelevitz, C.I. Henschke; Title: "Three–dimensional segmentation of solitary pulmonary nodules from helical CT scans"; *CARS '99 Computer Assisted Radiology and Surgery: Proceedings of the 13$^{th}$ International Congress and Exhibition,* pgs. 203–207; Date of Publication: 1999; Place of Publication: U.S.

Author: American Cancer Society: Title: "Cancer Facts & Figures 2002"; 1599 Clifton Road, NE, Atlanta, GA, 30329–4251.

Author: Claudia I. Henschke, D.P. Naidich, D.F. Yankelevitz, G. McGuinness, D.I. McCauley, J.P. Smith, D.M. Libby, M.W. Pasmantier, M. Vazquez, J. Koizumi, D. Flleder, N.K. Altorki, and O.S. Miettinen: Title: "Early Lung Cancer Action Project: Initial Findings on Repeat Screening"; Cancer Jul. 1, 2001; 92(1):153–159; Date of Publication: Jul. 1, 2001; Place of Publication: U.S.

Author: R. Kakinuma, H. Ohmatsu, M. Kaneko, K. Eguchi, K. Naruke, K. Nagai; Title: "Detection failures in spiral CT screening for lung cancer: analysis of CT findings"; Radiology 212, pp. 61–66; Date of Publication: 1999; Place of Publication: U.S.

Author: M. Remy Jardin, F. Giraud, C–H Marquett; Title: "Pulmonary nodules: detection with thick section spiral CT versus conventional CT"; Radiology, 187(No.2), pp. 513–520; Date of Publication: 1993; Place of Publication: U.S.

Author: S. H. Heywang–Koebrunner, B. Lommatzsch, et al.; Title: "Comparison of spiral and conventional CT in the detection of pulmonary nodules(abstract)"; Radiology, 185, 131; Date of Publication: 1992; Place of Publication: U.S.

Author: J. A. Buckley, W. W. Scott, S. S. Siegelman, et al.; Title: "Pulmonary nodules: effect of increased data sampling on detection with spiral CT and confidence in diagnosis"; Radiology, 196, pp. 395–400; Date of Publication: 1995; Place of Publication: U.S.

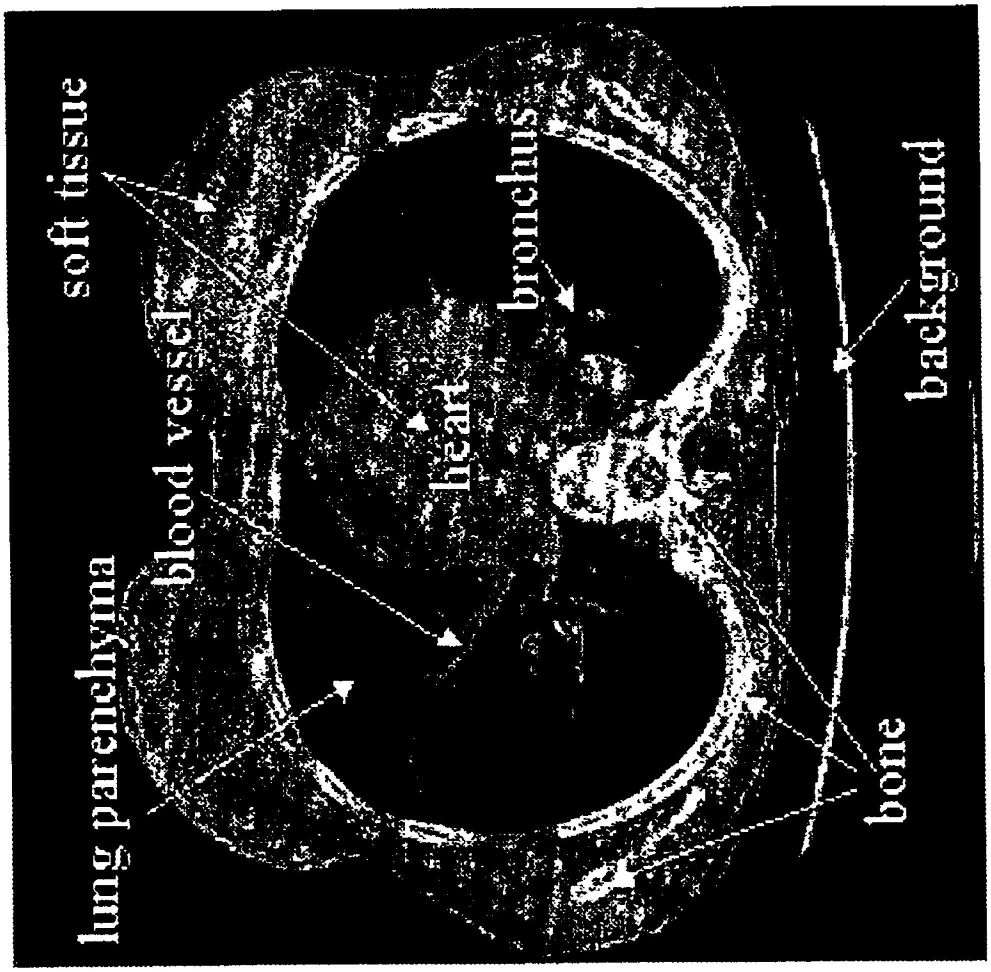
Fig. 2. One slice of a chest CT image series.

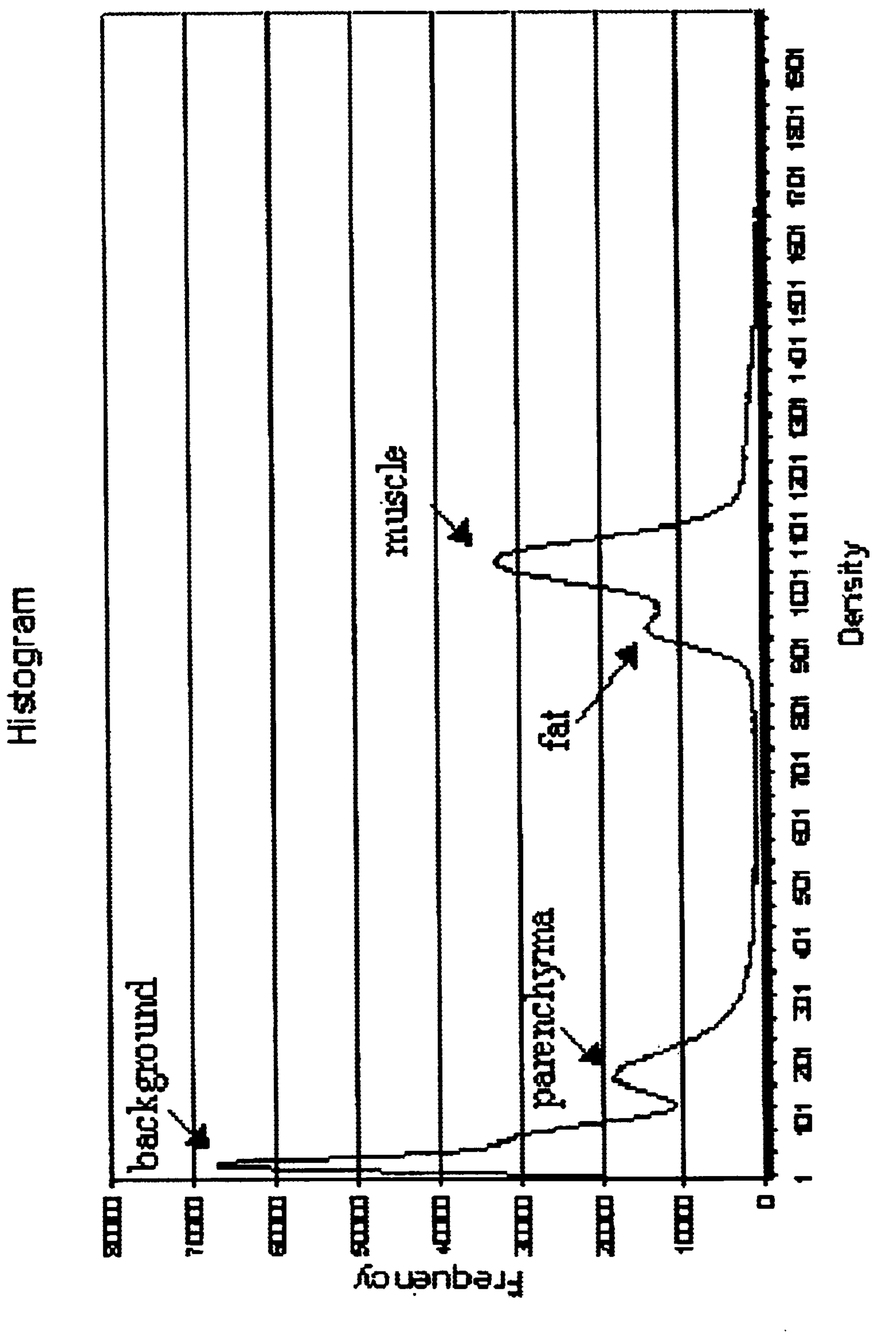
Fig. 3 Corresponding volumetric density histogram

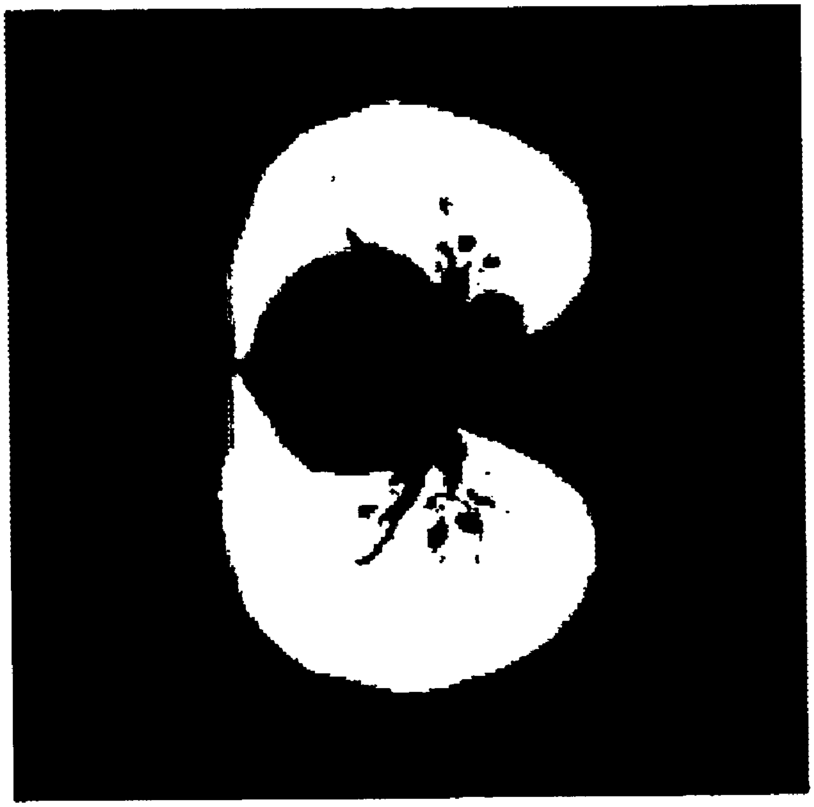
Fig. 5 Incomplete lung mask
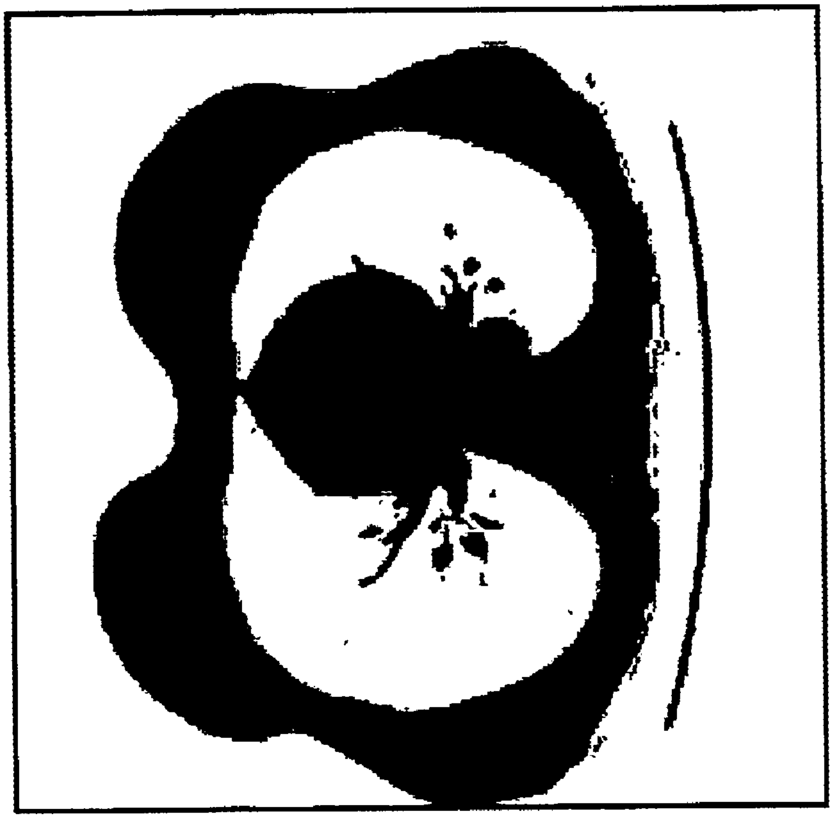
Fig. 4 Thresholded image (t=750)

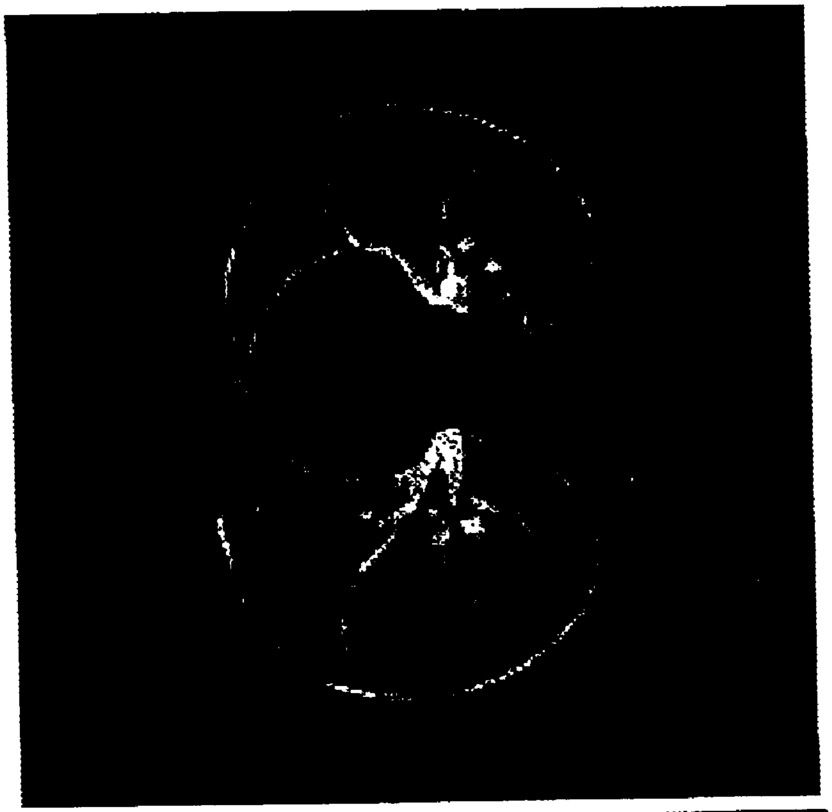
Fig. 7 Extracted lungs
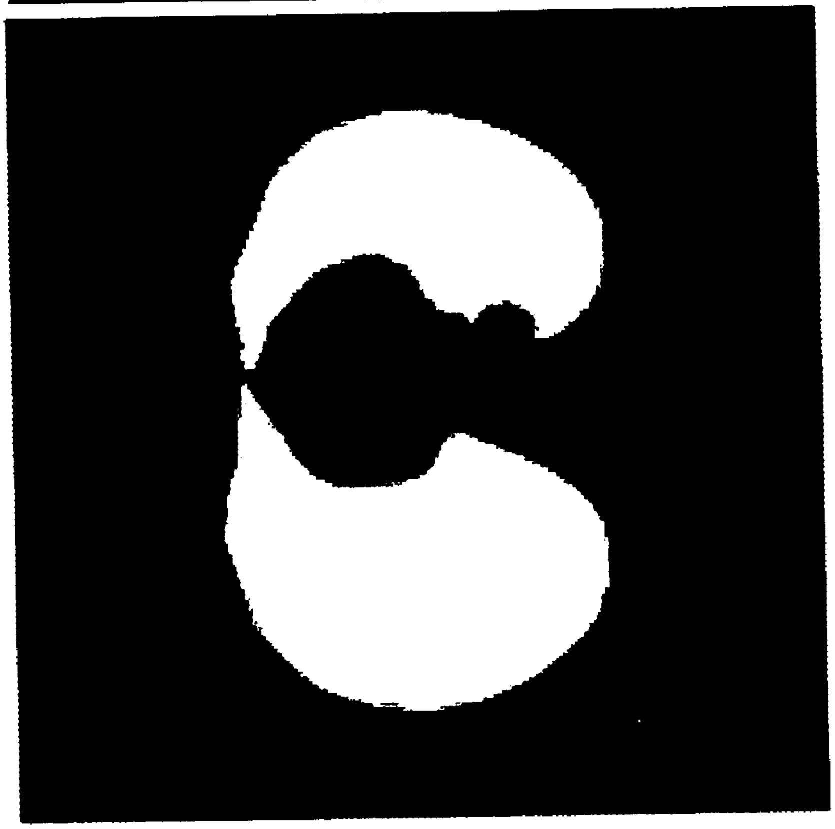
Fig. 6 Complete lung mask

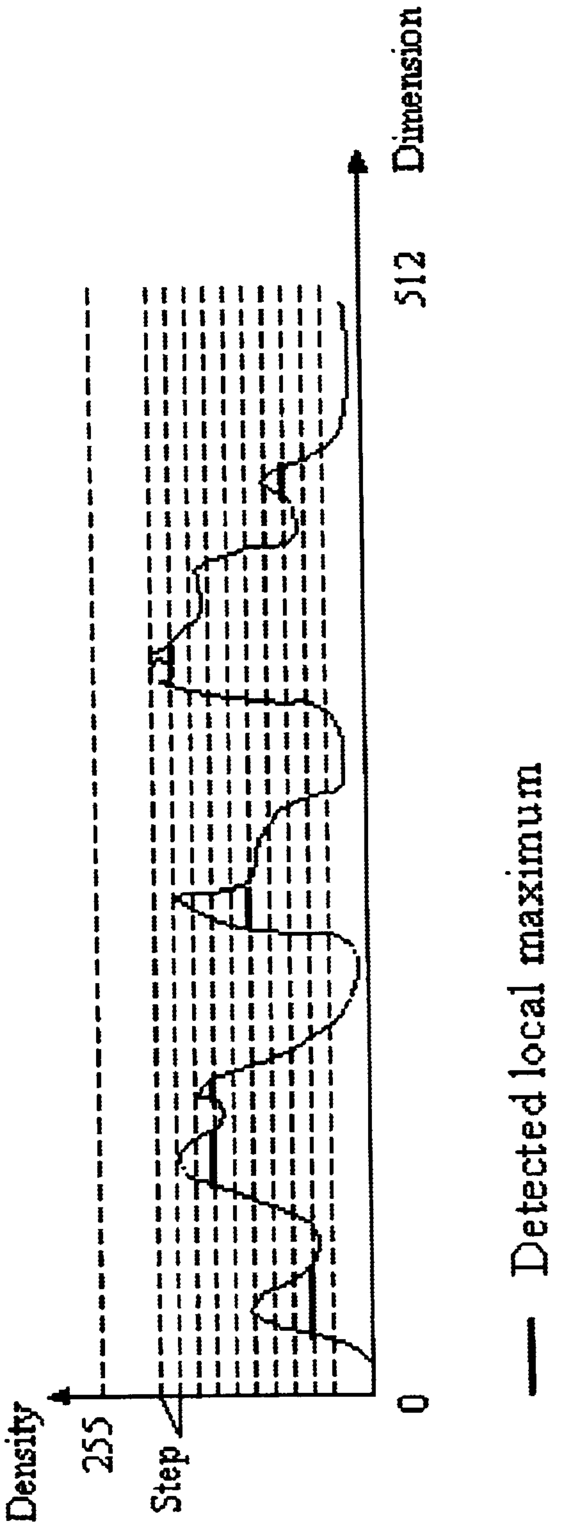
Fig. 8 Determination of local density maxima with an one-dimensional example

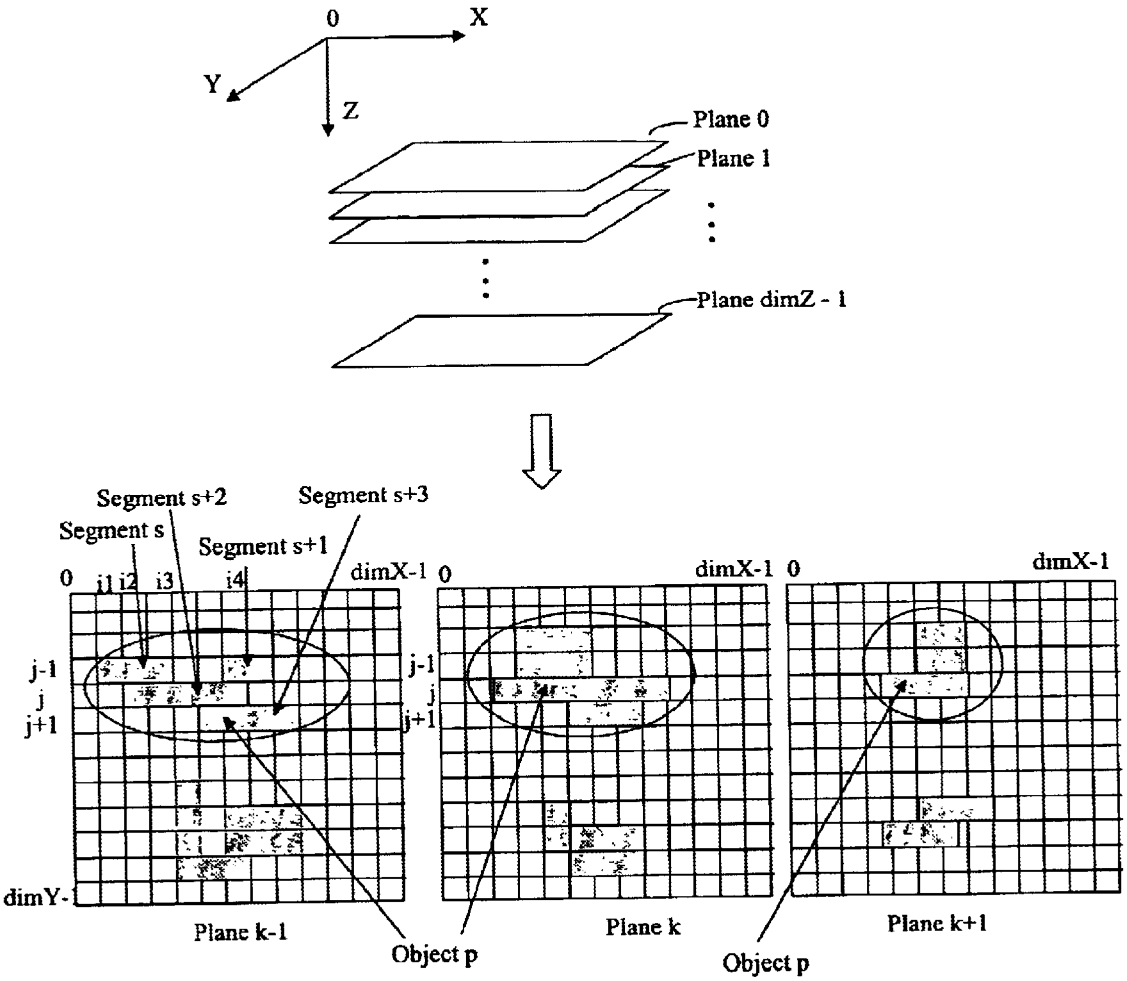

Segment s (in row j-1) overlaps segment s+2 (in row j) if the end point of segment s (column i3) is larger than the start point of segment s+2 (column i2) or the start point of segment s (column i1) is smaller than the end point of segment s+2 (column 4).

Segments s, s+1, s+2, s+3, and s+4 in the plane k-1 (within the circle) belong to the same object p. So as all segments in the circles in the plane k and k+1 because of their overlaps along the z direction.

FIG. 12

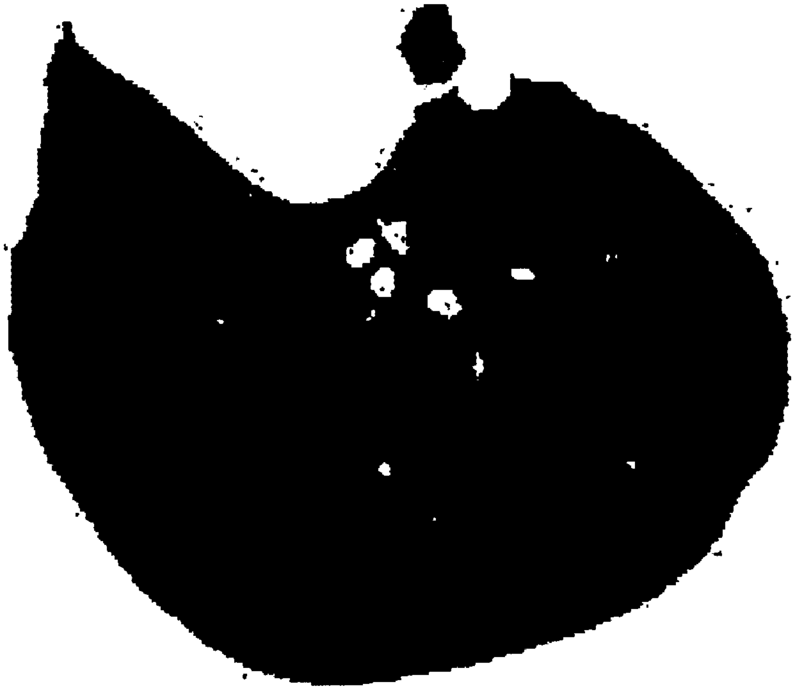
Fig. 14 Thr = 145
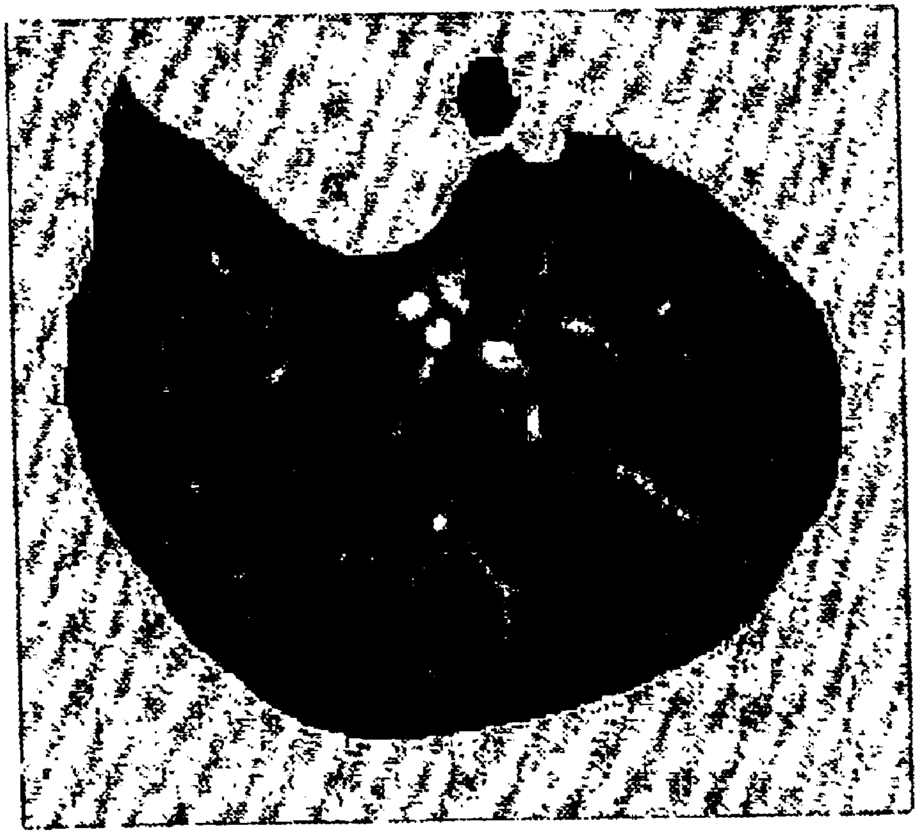
Fig. 13. Original image

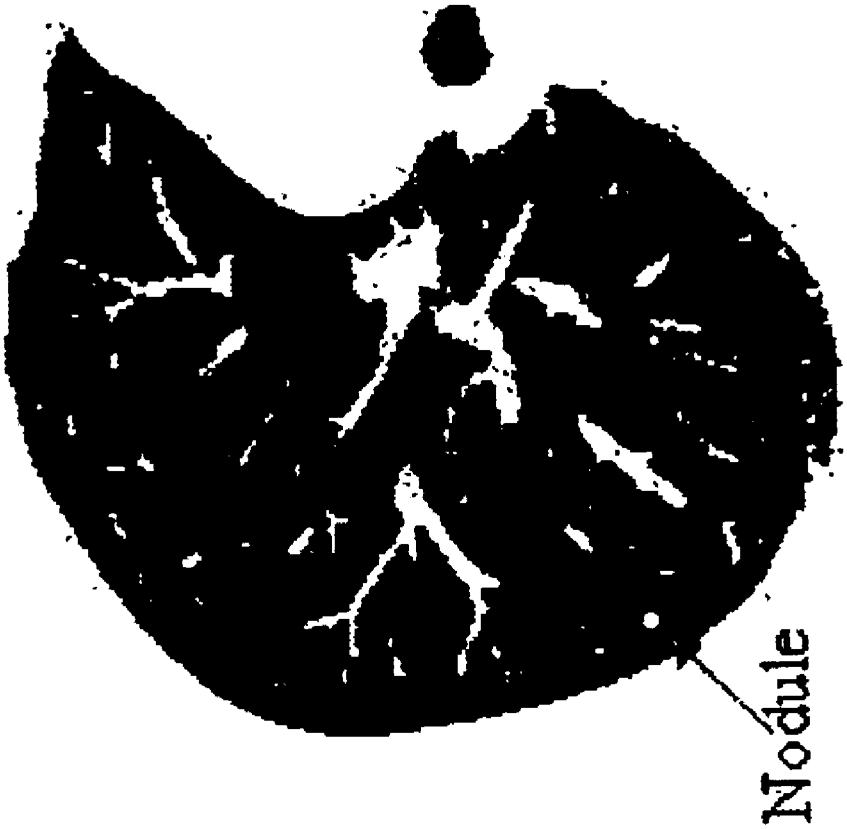
Fig. 16 Thr=70
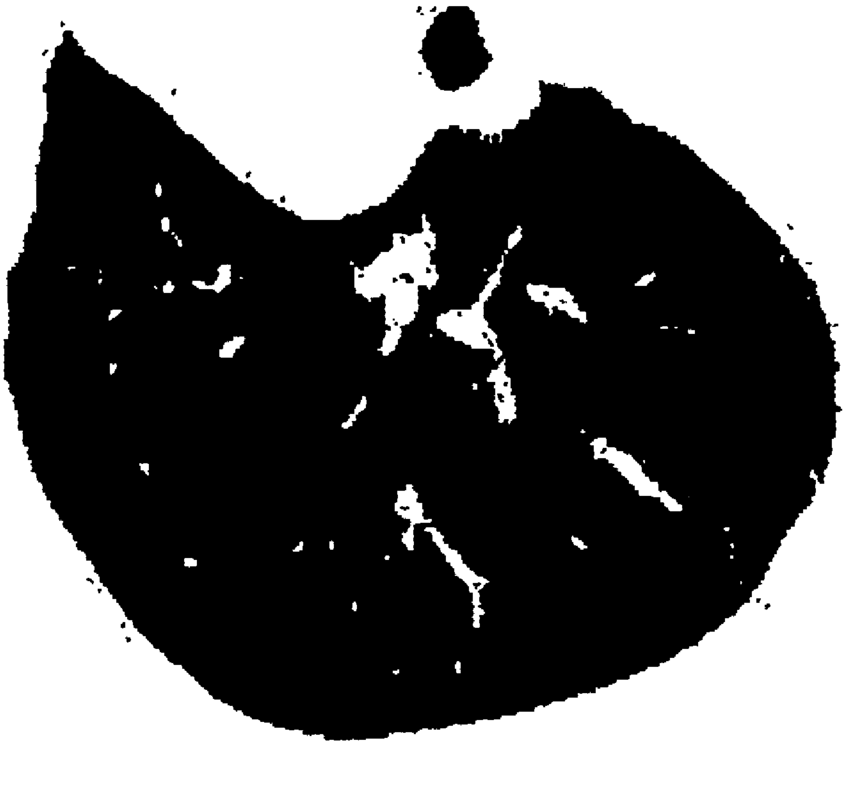
Fig. 15 Thr=90

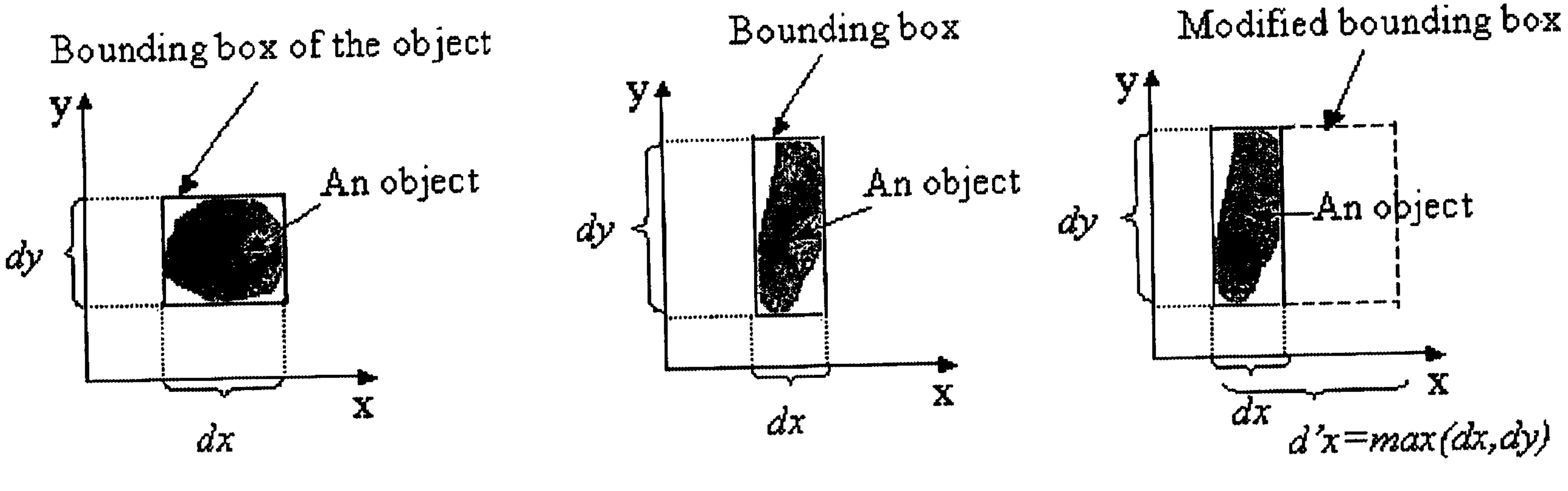

(a) (b) (c)

$R1$=number of object pixels / (max($dx$, $dy$) * max($dx$, $dy$))

Fig 17 Explanation of the modification of an object's bounding box in two dimensions Objects in (a) and (b) have very distinct shapes. If we use the bounding box to define the parameter of $R1$, i.e., $R1$=number of object pixels / ($dx$ * $dy$), the two objects will have similar values of $R1$. However, If we use the modified bounding box ((c)) to define the parameter of $R1$, i.e., $R1$=number of object pixels / (max($dx$,$dy$) * max($dx$,$dy$)), the two objects will have distinct values of $R1$.

AUTOMATIC DETECTION OF PULMONARY NODULES ON VOLUMETRIC COMPUTED TOMOGRAPHY IMAGES USING A LOCAL DENSITY MAXIMUM ALGORITHM

This application claims the benefit of U.S. Provisional Application No. 60/338,880 filed Oct. 24, 2001, which is incorporated herein by reference.

BACKGROUND OF THE INVENTION

The present invention is related to computer-aided analysis of lung nodules in medical images. In particular, the invention is directed to computer-aided review of computed tomography images for initially detecting lung nodule candidates for a subsequent analysis based upon the features of the lung nodule candidates.

Lung cancer is the leading cause of cancer deaths among the population in-the United States. Each year there are about 170,000 newly diagnosed cases of lung cancer and over 150,000 deaths. More people die of lung cancer than of colon, breast, and prostate cancers combined. Despite the research and improvements in medical treatments related to surgery, radiation therapy, and chemotherapy, currently the overall survival rate of all lung cancer patients is only about 14 percent. Unfortunately the survival rate has remained essentially the same over the past three decades. The high mortality rate of lung cancer is caused by the fact that more than 80% lung cancer is diagnosed after it has metastasized. Patients with early detection of lung cancer followed by proper treatment with surgery and/or combined with radiation and chemotherapy can improve their five-year survival rate from 13 percent to about 41 percent. Given that earlier-stage intervention leads to substantially higher rates of survival, it is therefore a major public health directive to reduce the mortality of lung cancer through detection and intervention of the cancer at earlier and more curable stages.

The development of the computed tomography (CT) technology and post-processing algorithms has provided radiologists with a useful tool for diagnosing lung cancers at earlier stages. However, current CT systems have their inherent shortcomings in that the amount of chest CT images (data) that is generated from a single CT examination, which can range from 30 to over 300 slices depending on image resolution along the scan axial direction, becomes a huge hurdle for the radiologists to interpret. Even though small lung nodules can be captured by helical CT and the images can be viewed in either a traditional film-based mode or cine mode on today's Picture Archiving and Communication System (PACS) workstations, the potential of overlooking small nodules in the diagnostic process has become major concerns.

Accordingly there is a need for a system that automatically identifies small lung nodule candidates from helical CT images to assist radiologists in improving the detection of nodules in the clinical practice.

SUMMARY OF THE INVENTION

The present invention is a method and apparatus for analyzing volumetric chest computed tomography images for lung nodules. The steps of the method of the invention include initially obtaining the volumetric chest computed tomography images for lung nodules from an image acquisition device. The lungs are then separated from the other anatomic structures on the images to form lung images. The lung images are then processed to detect nodule candidates with a local density maximum algorithm. False-positives among the detected nodule candidates are then reduced by an application of parameters concerning lung nodules. Preferably the parameters concern at least the size and shape of the nodule candidates.

The present invention similarly includes an article of manufacture for analyzing volumetric chest computed tomography images for lung nodules. The article includes a machine readable medium containing one or more programs which when executed implement the method of the invention.

For a better understanding of the present invention, reference is made to the following description to be taken in conjunction with the accompanying drawings and its scope will be pointed out in the appended claims.

BRIEF DESCRIPTION OF THE DRAWINGS

Preferred embodiments of the invention have been chosen for purposes of illustration and description and are shown in the accompanying drawings, wherein:

FIG. 2 is an illustration of a slice of a typical chest CT image series obtained with General Electric LightSpeed QX/i;

FIG. 3 is an illustration showing the volumetric density histogram of the image series of which one slice is shown in FIG. 2;

FIG. 4 is an illustration showing the original slice shown in FIG. 2 thresholded at t=750 gray level;

FIG. 5 is an illustration showing an incomplete lung mask for the original slice shown in FIG. 2;

FIG. 6 is an illustration showing the complete lung mask for the original slice shown in FIG. 2;

FIG. 7 is an illustration showing the extracted lungs from the original slice shown in FIG. 2;

FIG. 8 is an illustration showing a one dimensional example of the detection of local density maxima;

FIG. 12 is an illustration showing the three dimensional relationship of the binary image data;

FIG. 13 is an illustration showing an extracted lung image;

FIG. 14 is an illustration showing the extracted lung image shown in FIG. 13 thresholded at a level of 145;

FIG. 15 is an illustration showing the extracted lung image shown in FIG. 13 thresholded at a level of 90;

FIG. 16 is an illustration showing the extracted lung image shown in FIG. 13 thresholded at a level of 70; and FIG. 17 illustrates modification of an object's bounding box when applying parameters concerning lung nodules.

DETAILED DESCRIPTION OF THE INVENTION

Figure 1:
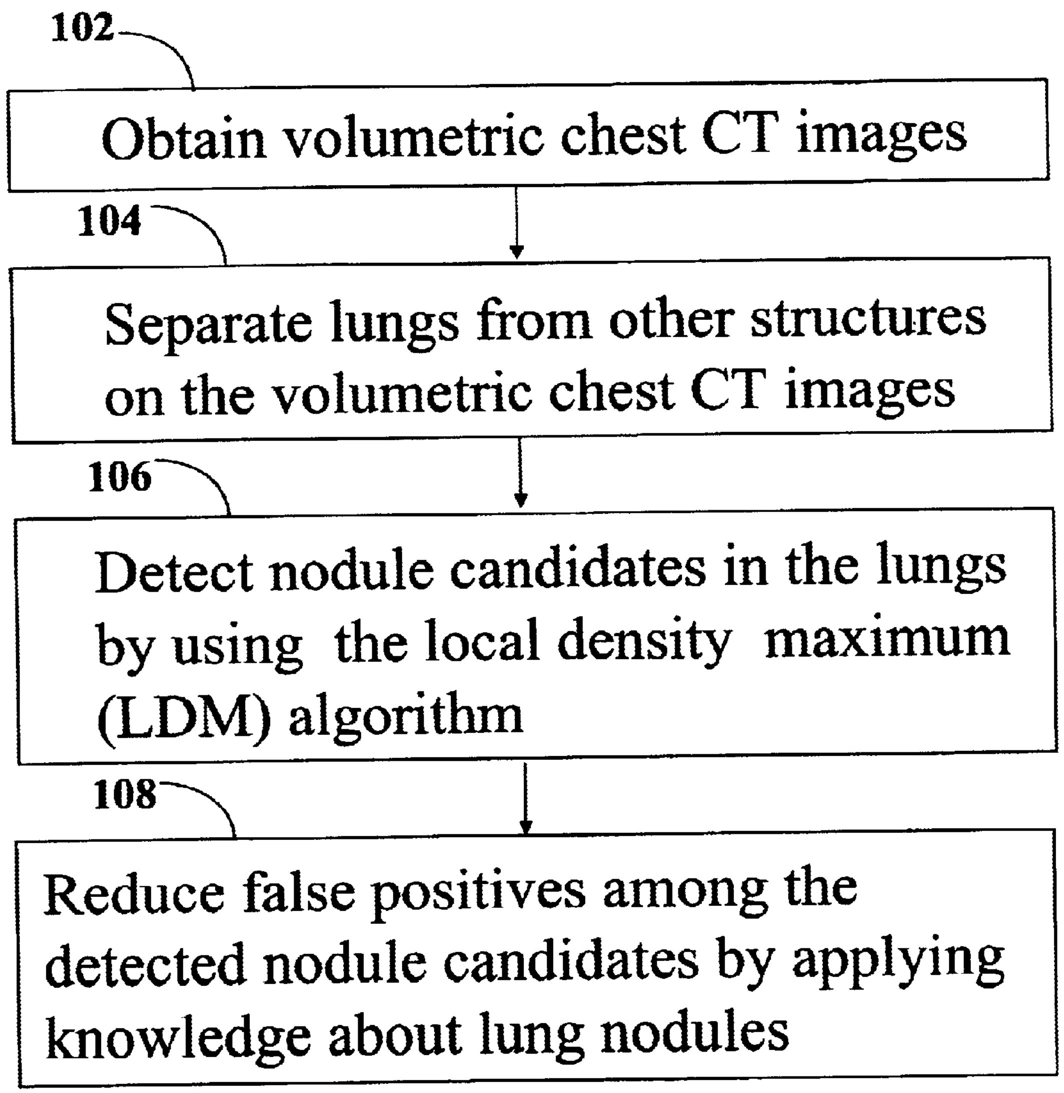
FIG. 1 is a flowchart illustrating the process of examining a patient using computed tomography (CT) technology in accordance with the present invention.

Referring to FIG. 1, a flowchart illustrating the process of examining a patient using the computed tomography (CT)

technology in accordance with the present invention is depicted. The initial step 102 is to obtain the volumetric chest CT images of the patient. Preferably the images are acquired helically using a standard clinical protocol and the image data is transferred to and stored on a standard local computer for further processing. Suitable scanners for obtaining the images include General Electric HighSpeed CT/i and LightSpeed QX/i. The image data can be transferred via an Ethernet and the computer can be a personal computer or a UNIX machine. The next step 104 is to separate the lungs from the other anatomic structures on the volumetric chest CT images. The separation of the lungs 104 is explained in detail below with reference to FIGS. 2 through 7. Similar techniques to extract the lungs from CT chest images can be found elsewhere (Shiying Hu, Eric A. Hoffman, and Joseph M. Reinhardt, "Automatic Lung Segmentation for Accurate Quantitation of Volumetric X-Ray CT images". IEEE Transactions on Medical Imaging, Vol. 20, No. 6, June 2001; Li Fan, Carol L. Novak, Jiangzhong Qian, Gerhard Kohl, and David P. Naidich, "Automatic Detection of Lung Nodules from Multi-Slice Low Dose CT Images". Proc SPIE 2001; 4322:1828–1835.). After the lungs are separated, the next step 106 is to detect nodule candidates using a local density maximum algorithm in accordance with the present invention. The final step 108 is to reduce false-positives among the nodule candidates by analyzing the characteristics of the detected nodule candidates. Features that can distinguish spherical shape (nodules) from cylinder shape (vessels and bronchi) such as three-dimensional compactness factor (Binsheng Zhao, Anthony Reeves, David Yankelevitz, and Claudia Henschke, Three-dimensional multi-criterion automatic segmentation of pulmonary nodules of helical CT images. Optical Engineering 1999; 38(8):1340–1347, which is incorporated herein by reference) can be used to delete false positive results.

Referring initially to FIG. 2, a slice of a typical chest CT image series obtained with General Electric LightSpeed QX/i is shown while the corresponding volumetric density histogram is shown in FIG. 3. The histogram illustrates that there are typically four peaks around the mean density values representing, from left to right, the background outside the body but within the scan area, lung parenchyma, fat, and muscles. The histogram also includes a long, flat and low valley between the peaks of the lung parenchyma and the fat. The presence of the valley within the histogram indicates that the separation of the parenchyma from the soft tissues and bones is generally insensitive to a threshold set within the valley. This characteristic is useful in extracting or separating the lungs from the other structures on the volumetric chest CT images in accomplishing step 104 as shown in FIG. 1.

The extraction of the lungs from the other anatomic structures generally involves initially selecting a threshold value lying in the valley close to the peak of the fat to initially separate lung parenchyma and the background from the soft tissues and bones as shown in FIG. 4. In FIG. 4, a threshold value of 750 gray level (All values of gray level obtained from the GE Lightspeed QX/i machine equate to Hounsfield units HU as follows: gray level=HU+1024, for example 1000 gray level=−24 HU.) was selected to extract the soft tissues and bones. Voxels having density lower than the threshold value will be recognized as lung candidates and assigned the value of one and appear white in FIG. 4, whereas other voxels assigned the value of zero in the resultant image appear black in FIG. 4. In comparing FIG. 4 with FIGS. 2 and 3, the soft tissues and bones which have voxel densities greater than the threshold value appear black while the background and lung parenchyma which have voxel densities lower than the threshold value appear white.

The lung parenchyma is next separated from the background by initialing labeling connected voxel components. The voxel components are labeled by finding geometrically connected voxels that have the value of one in the thresholded binary images and assigning an identical number to each individual group of the connected voxels. The largest component that does not touch any margin of the images is selected next as shown in FIG. 5. Since the apparent densities of vessels and bronchi in the lungs vary widely, regions in the lungs with higher densities generally get grouped into soft tissues and bones causing an incomplete extraction of the lung mask as shown in FIG. 5. To obtain a complete lung mask (i.e., to include those high-density segments of vessels and bronchi as well as nodules into the parenchyma group) a morphological dilation followed by an erosion of the result is applied as shown in FIG. 6. The lung mask is used to extract the lung regions as shown in FIG. 7 from the original chest CT images shown in FIG. 2. After the extraction, the resulting images are referred to lung images. The lung images are preferably converted from the image type of short (16 bits) to the type of byte (8 bits) by a linear projection for further processing.

Referring initially to FIG. 8, the detection of lung nodules using a local density maximum algorithm is illustrated in a one-dimensional example. The illustration in FIG. 8 represents a plot of the voxel density along the length of a cut through one plane of volumetric data which would appear as a single image similar to that which is shown in FIG. 2. In FIG. 8, six (6) local maxima are represented by the individual peaks in the plot which signify the detection of a nodule candidate for each peak. The local maxima are detected in the volumetric data in a dynamic thresholding manner which is described below with reference to the flowcharts shown in FIGS. 9, 10A, 10B, and 11, and FIGS. 13 through 16.

Figure 9:
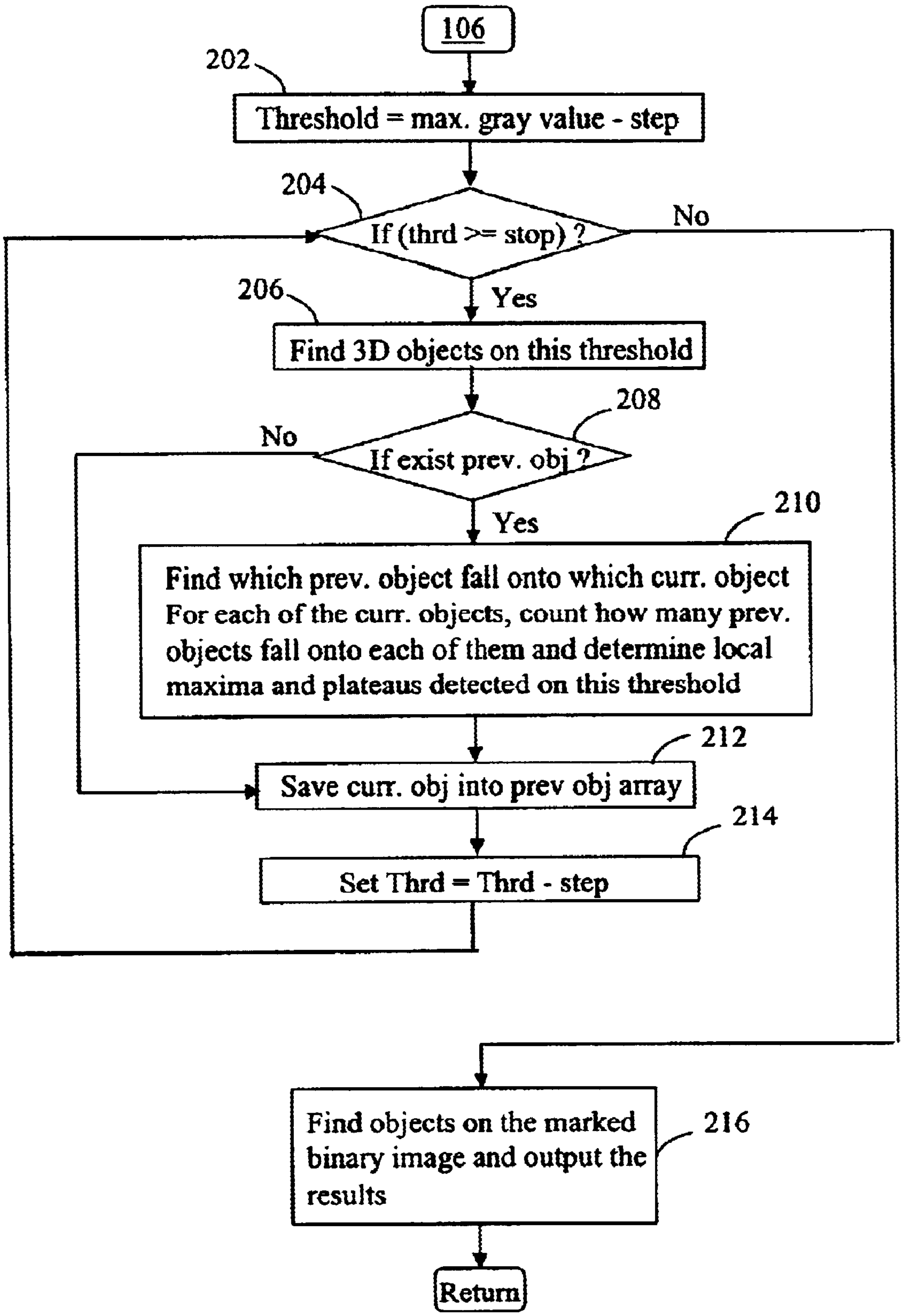
FIG. 9 is a flowchart of the main loop of the local density maximum algorithm for detecting lung nodules.

Referring now to FIG. 9, the main loop of the algorithm for the detecting nodule candidate step 106 using a local density maximum algorithm is illustrated. The lung images are segmented using an initial threshold determined at step 202. At step 202, the initial threshold level is set to a value equal to the maximum voxel density value of the lung images minus a predefined threshold step value. The step value is illustrated in FIG. 8 and is preferably selected within a range between about 5 and 10 (in gray level). The step value selected for generating the images included in this application was 7 (in gray level). At step 204, the current threshold value is compared against a predefined stop value to determine whether further processing is required. The stop value can be set as low as 0, but is preferably set at about 15 (in gray level). If the threshold value is greater than the predefined stop value, the processing proceeds to step 206 to find 3D objects at this threshold level. Otherwise, the results of the algorithm will be output for further processing at step 108 as shown in FIG. 1. When step 206 is processed, the binary image that results from the current threshold value is processed to identify three-dimensional (3D) objects that are represented by geometrically connected voxels having a value of one. The details of step 206 are explained in more detail below with reference to FIGS. 10A and 10B. At step 208, it is determined whether a previous object had been detected. During the first loop when the threshold value is equal to the initial threshold value set in step 202, there is never a previous object. If no previous object is detected, the current object or objects are saved to a previous object array (step 212) and the current threshold value is reduced by the step value at step 214 and the processing loops back to step 204 for repeating steps 204 through 214 as long as the criteria at step 204 is satisfied as discussed above. If there are previous objects at step 208, the processing proceeds to step 210 for a determination of local maxima at the current threshold value based on the analysis of the relationship between previous and current objects and the criteria of being a local maximum. The details of step 210 are explained below with reference to FIG. 11. The processing continues with step 212 as described above.

Referring now to FIGS. 13 through 16, the concept of the dynamic thresholding of the volumetric data is illustrated in a two dimensional view of extracted lung images that are subsequently thresholded at different threshold values to form binary images. In particular, FIG. 14 shows the original extracted lung shown in FIG. 13 being thresholded at a voxel density level of 145 (in gray level). At the threshold level of 145, at least all voxel data having a density level greater than 145 is assigned the value 1 and appear as white spots in FIG. 14. As the threshold value is reduced in FIGS. 15 and 16, more objects are identified. The actual identification of current and previous objects is a three dimensional analysis which is detailed in the flowchart in FIGS. 10A and 10B and is illustrated in FIG. 12.

Figure 10A:
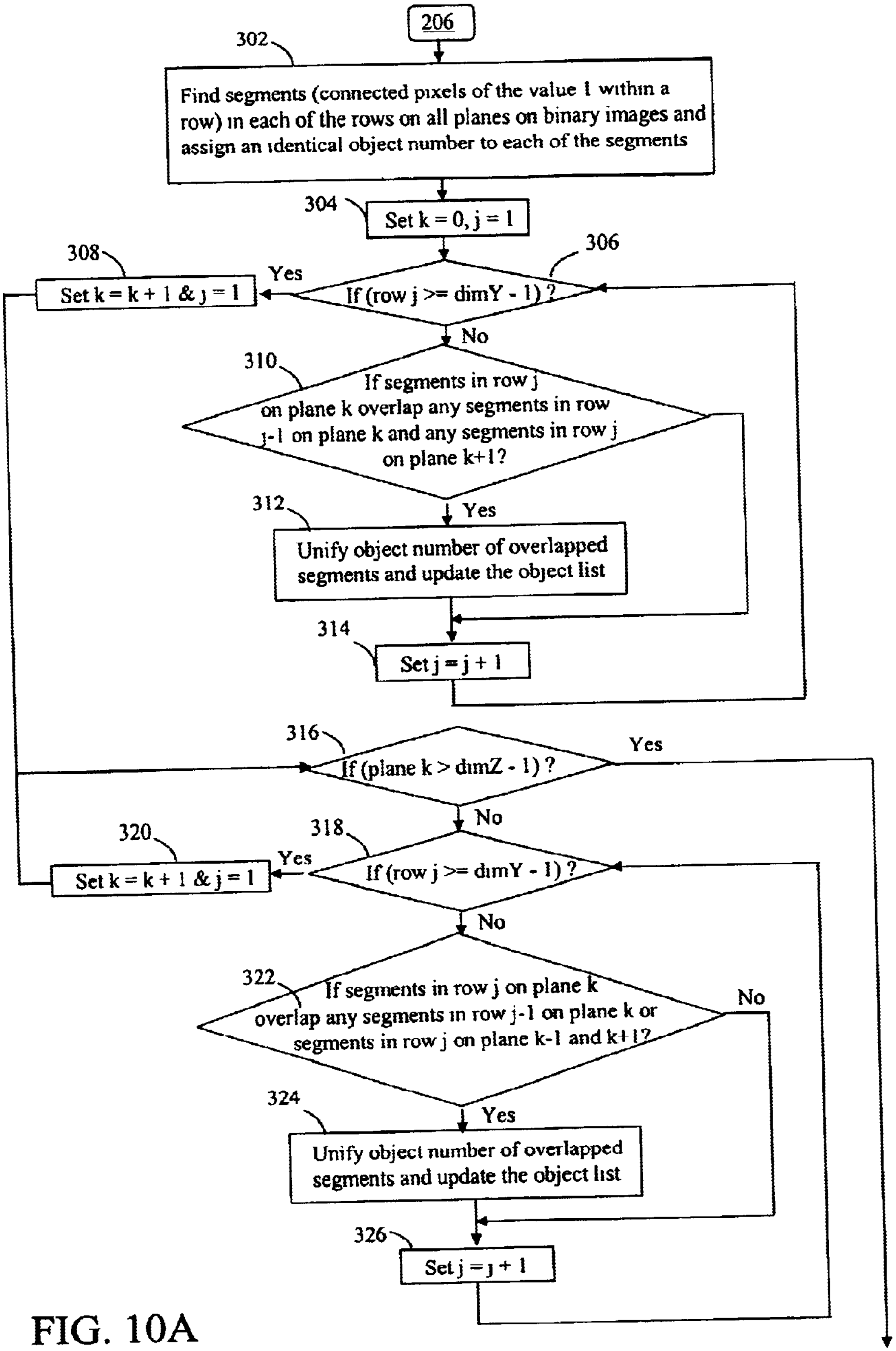
FIGS. 10A and 10B is a flowchart illustrating details on finding objects at a threshold level.
Figure 10B:
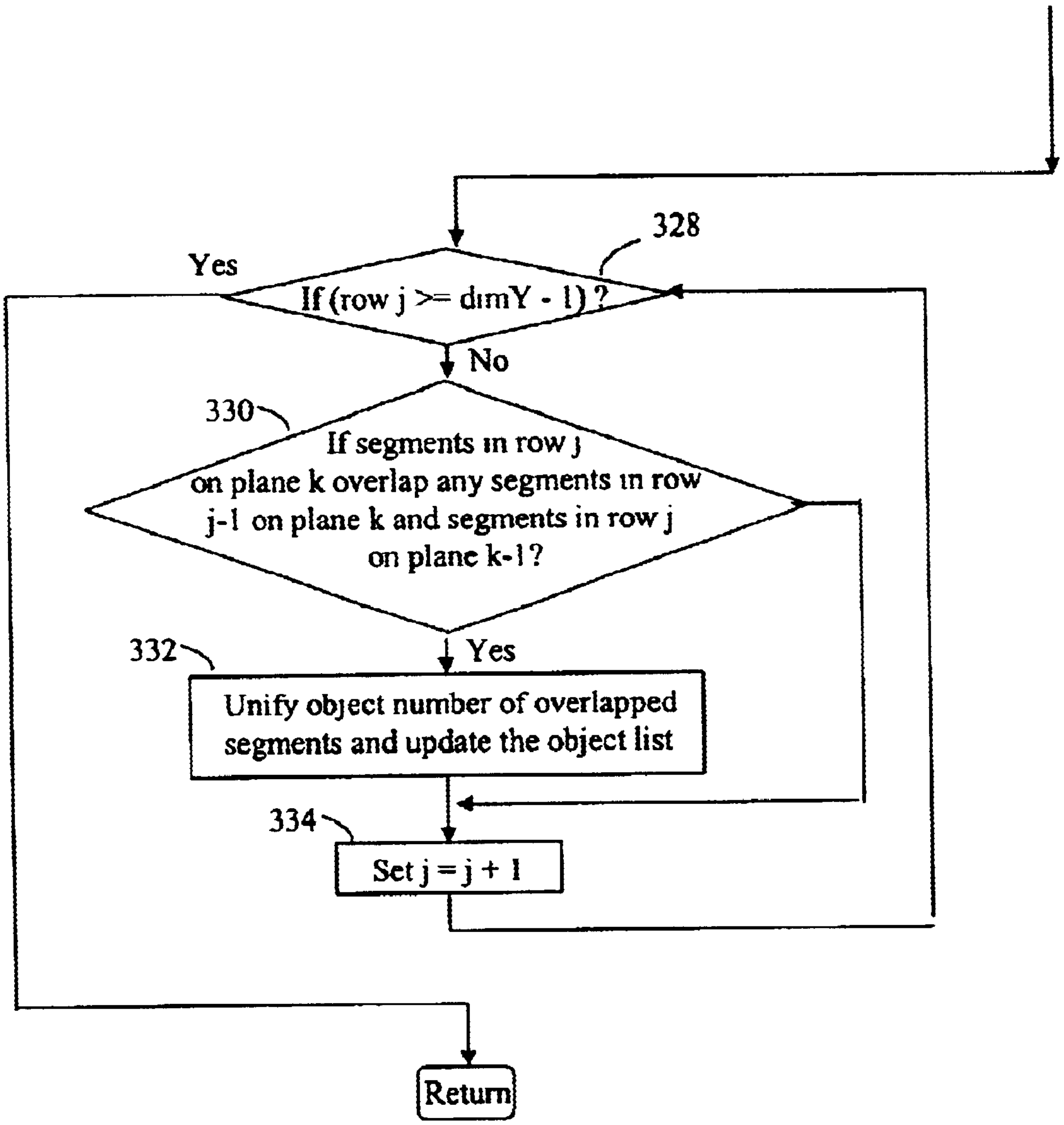

Referring now to FIGS. 10A, 10B, and 12, in step 206 the binary image that results from the current threshold value is processed to identify three-dimensional (3D) objects that are represented by geometrically connected voxels having a value of one. In step 206, the volumetric binary data is analyzed for segments which are connected pixels having a value of 1 in a row and assigning an object number to each segment. In FIG. 12, object "p", which is shown encircled, illustrates a single object that is present on planes k−1, k, and k+1. Where two segments overlap in three dimensions, the object number is unified.

Referring now to FIGS. 10A and 10B, the loop in step 206 starts from the first plane (k=0) and the second row (j=1) 304 on the first plane. Next at step 306, if it is beyond the last row on the first plane, the processing of the next plane (k=k+1) is initiated again at the second row (j=1) 308 on the new plane. If the processing has not completed the last row on the first plane, an analysis 310 is made to check Whether there exists any overlap between segments in row j and row j−1 on the plane k and segments in row j on the plane k+1. The object number is unified when there is an overlap 312. This process repeats 314 until all of the rows in the current plan are processed. Once the processing is completed for a plane, the next plane is similarly processed starting from the first row on the new plane. In summary, each time in the processing of step 206 the binary volumetric data is iteratively processed to find three dimensional objects.

Figure 11:
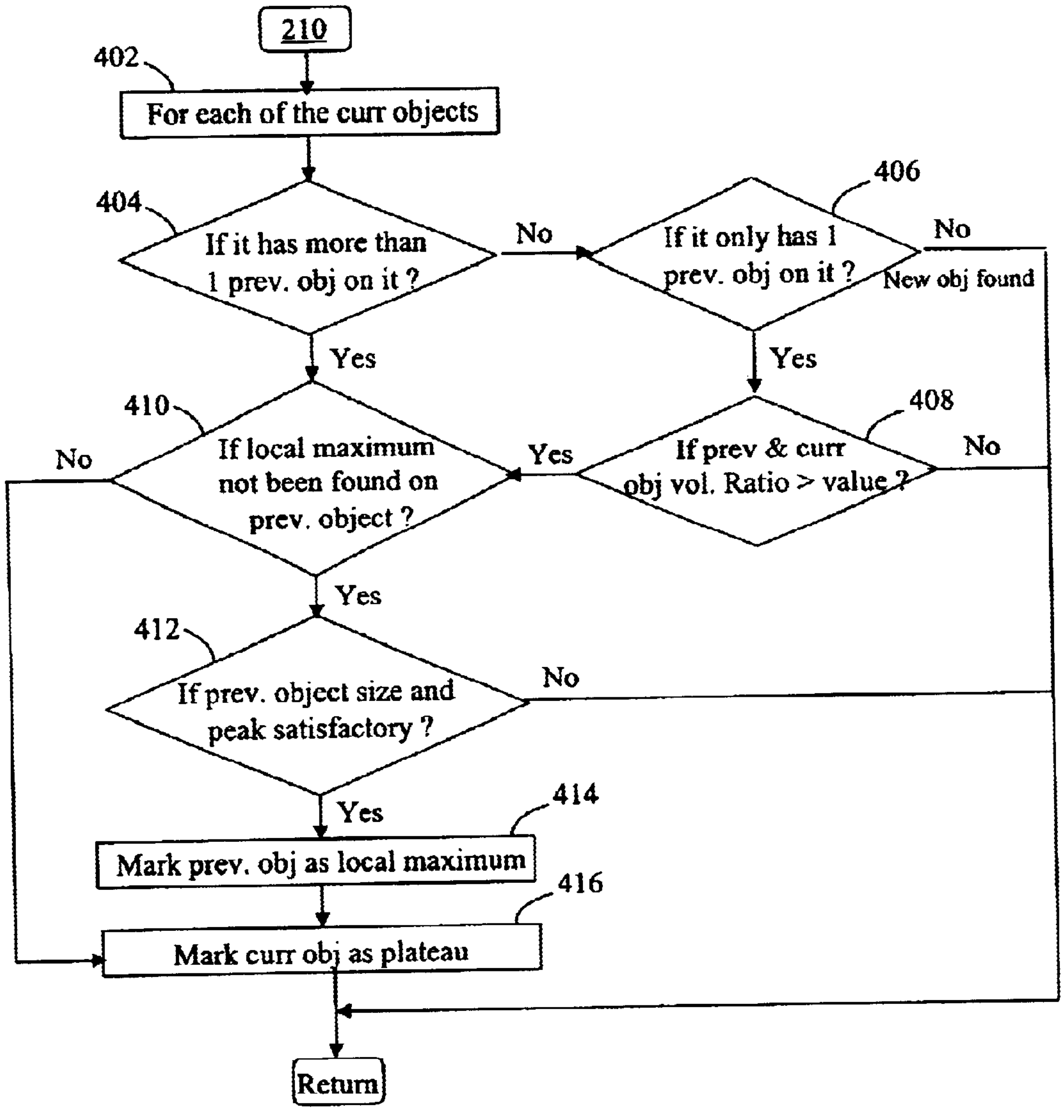
FIG. 11 is a flowchart illustrating details for determining the local maxima at the current threshold value based on the analysis of the relationship between previous and current objects and the criteria of being a local maximum on finding objects at a threshold level.

Referring now to FIG. 11, in step 210 a determination of local maxima at the current threshold value is performed based on the analysis of the relationship between previous and current objects and the criteria of being a local maximum. Since the objects are composed of segments, the analysis is actually performed on the basis of segments. For each current object an initial determination 404 is made as to whether it has more than 1 previous object on it. If the object has more than one previous object on it, a determination 410 as to whether local maxima have already been found on this object is made. When local maxima have already been found on this object, the current object is marked as a plateau 416. Otherwise when there have not been any local maxima found on this object, an analysis 412 is conducted to determine whether any of the previous objects meet the criteria of being a local maximum. If the criteria of being a local maximum is met, the previous object is marked as a local maximum 414. The criteria for being a local maximum preferably include size and density. The size requirements are preferably defined so that the object must be larger than a range from about 15 to 25 voxels, and most preferably about 20 voxels to be considered a local maximum. The density is preferably defined so that the object must be significantly higher than the current threshold level to be considered a local maximum. Generally, the difference between the two densities must be greater than 12 (in gray level). If a local maximum is determined, the object containing these local maxima will be interpreted as a plateau 416.

If the object at step 404 does not have more than 1 previous object on it, then a determination 406 is made as to whether there is only one previous object on the current object. When there is no previous object on the current object a new object is detected and is registered as an object detected at this threshold value. When there is only 1 previous object on the current object, the object-to-box ratios (defined as the ratio of the size of the object to the size of the rectangular box that contains the object) of current and previous objects are checked 408 to determine whether the ratio of the object-to-box ratio of the previous object to that of the current object is larger than a specified value. The specified value can range between about 25 and 35 and is preferably selected to be 30. The current object will replace the previous one provided the specified value is not exceeded. Otherwise, the previous object will be recognized as a local maximum and the current object will be recognized as a plateau.

Referring now to FIG. 1, after step 106 is completed to detect the local density maxima in the lungs, false-positives are reduced in step 108 from the nodule candidates by applying knowledge known about the lung nodules. Only the local maxima falling into the interesting range of nodule size (about 2 mm<diameter<about 20 mm) will be reserved. Although a nodule on a CT slice can appear to be similar to a vessel that is perpendicular to the slice, nodules and vessels have very discriminating shapes in three dimensions; the former have a spherical shape, whereas the latter have a tubular shape. The following ratios are calculated to determine the "three-dimensional compactness factor" of an object. The ratios include at least the following:

1) the ratio of the size of the object to the size of the rectangular box that contains the object (always smaller than 1.0); and 2) the ratio of the object lengths along x, y and z axes.

If the first ratio is larger than about 0.4, the object is considered to be compact. If the second ratio of max(object length along x axis, object length along y axis) to min(object length along x axis, object length along y axis)<about 1.5 and the ratio of object length along z axis to min(object length along x, object length along y axis)<about 2, the object is considered to be compact. The latter ratio is set slightly larger than the former ratio because of the partial voxel effect caused by the non-isotropic CT images in three directions. By calculating the object length along z axis, the non-isotropic character of CT images need to be taken into consideration.

In a preferred embodiment, only the local maxima falling into the interesting range of nodule size (about 2 mm<diameter<about 20 mm) is reserved, and the following ratios are calculated to determine the shape compactness of an object. The ratios include at least the following:

1) R1 is defined as the ratio of the volume of the object to the volume of a modified bounding box of the object, i.e., $$R1=\text{number of object voxels}/(\max(dx,\ dy)^*\max(dx,\ dy)^*dz) \qquad (1)$$

where, dx, dy and dz are the maximal projection lengths (in pixel) of the object along the axes of x, y and z, respectively, and max(dx, dy)=dx, if dx>=dy; otherwise, max(dx, dy)=dy. The volume of the box containing an object is given by the denominator in Eq. (1) rather than by dx*dy*dz which is the volume of the bounding box of the object. The modification of the bounding box in x-y plane allows R1 to be able to distinguish between a compact-shaped object from a stick-like object lying in the lungs at a small angle to either x or y coordinate axis. Similar modifications could have been made in x-z and y-z planes. However, they are ignored because with original CT data sets the resolution in axial (z) direction is almost 10-time lower that that in x or y direction and an object's dz is thus much smaller that dx or dy. FIG. 17 explains the modification of the bounding box of an object in two dimensions.

2) R2 is defined as the ratio of the maximal projection length of the object along the axis of z to the maximal projection length of the object along the axis of x or y whichever is larger. In-isotropic characteristic of CT scan is taken into account by multiplying the length (in pixel) by the corresponding pixel size.

$$R2=dz^*\text{psize\_z}/(\max(dx,\ dy)^*\text{psize\_x}) \qquad (2)$$

where psize_z and psize_x (=psize_y) are the pixel sizes (in mm) along z and x (y) directions, respectively.

3) R3 is defined as the ratio of the maximal projection length of the object along the axis of x or y whichever is larger to the maximal projection length of the object along the axis of x or y whichever is smaller.

$$R3=\max(dx,\ dy)/\min(dx,\ dy) \qquad (3)$$

where min(dx, dy)=dx, if dx<dy; otherwise, min(dx, dy)=dy.

An object (nodule candidate) will be considered as non-compact or not within the size range of interest, and thus be deleted if the following expression is true.

$$R1<\text{about } 0.3\ \|R2>\text{about } 5.0\ \|R2<\text{about } 0.2\ \|R3>\text{about } 1.5\ \|((dx^*\text{psize\_x}<\text{about } 2.0)\&\&(dy^*\text{psize\_y}<\text{about } 2.0))\|\text{number of object voxels}>\text{about } 800 \qquad (4)$$

Where "||" is the logical "OR" and "&&" is the logical "AND". The threshold values for R1, R2, and R3 are determined experimentally. The above-defined parameters and conditions ensure that the remaining objects have relatively compact shapes in three dimensions (R1<about 0.3), two dimensions (R2>about 5.0, R2<about 0.2, and R3>about 1.5), and fall into the size range of nodule of interest (about 2 mm<diameter<about 8 mm). Although in-isotropic character of a CT scanner is taken into account while calculating the parameter of R2, the threshold level of R2 is deviated from one (1) (the closer the value of R2 to one, the more compact shape an object has). This is because the partial volume effect along the axis of z is larger than that along the axis of x or y.

In addition to the above-mentioned parameters and conditions, there is at least one more situation that needs to be considered, e.g., if a nodule is attached to surrounding vessel(s). In these cases the object should not be deleted even if Equation (4) is true, provided that the object shows a compact shape on one slice, and its segments projected on the axes x and y on this slice are larger than 5 mm but smaller than 30 mm. All threshold levels in Equation (4) are determined experimentally.

The present invention can be implemented using a conventional general purpose digital computer or microprocessor programmed according to the teachings of the present specification, as will be apparent to those skilled in the computer art. Appropriate software coding can readily be prepared by skilled programmers based on the teachings of the present disclosure, as will be apparent to those skilled in the software art. The inventor conducted experimentation with a form of the invention that was written in the C programming language.

The present invention includes a computer program product which is a storage medium including instructions which can be used to program a computer to perform processes of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

Stored on any one of the above described storage media (computer readable media), the present invention includes programming for controlling both the hardware of the computer and for enabling the computer to interact with a human user. Such programming may include, but is not limited to, software for implementation of device drivers, operating systems, and user applications. Such computer readable media further includes programming or software instructions to direct the general purpose computer to perform tasks in accordance with the present invention.

The programming of general purpose computer may include a software module for digitizing and storing images obtained from the image acquisition device (computed tomography scanner). Alternatively, it should be understood that the present invention can also be implemented to process digital data derived from images obtained by other means.

The invention may also be implemented by the preparation of application specific units such as integrated circuits or by interconnecting an appropriate network of conventional component circuits, as will be readily apparent to those skilled in the art.

Thus, while there have been described what are presently believed to be the preferred embodiments of the invention, those skilled in the art will realize that changes and modifications may be made thereto without departing from the spirit of the invention, and is intended to claim all such changes and modifications as fall within the true scope of the invention.

What is claimed is:

1. A method for analyzing volumetric chest computed tomography images for lung nodules, said method comprising the steps of:

obtaining the volumetric chest computed tomography images for lung nodules from an image acquisition device;

separating the lungs from other structures on the volumetric chest computed tomography images to form lung images;

detecting nodule candidates in the lung images with a local density maximum algorithm; and reducing false-positives among the detected nodule candidates based upon by an application of parameters concerning lung nodules.

2. A method as defined in claim 1, wherein: the parameters include for each nodule candidate are:

a number of voxels associated with the nodule candidate;

ratio R1 defined as a volume of the nodule candidate over a volume of a modified bounding box of the nodule candidate;

ratio R2 defined as a maximal projection length of the nodule candidate along an axis of z over a maximal projection length of the nodule candidate, the maximal projection length being the larger of a projection length along the axis of x and a projection length along axis of y; and ratio R3 defined as the maximal projection length of the nodule candidate over the minimal projection length, the minimal projection length being the smaller is smaller the projection length along the axis of x and the projection length along axis of y; and deleting the nodule candidate from further consideration when one of the following criteria is established:

R1 is less than about 0.3;

R2 is greater than about 5.0;

R2 is less than about 0.2;

R3 is greater than about 1.5;

((the projection length along the axis of x is less than about 2.0 mm) AND (the projection length along axis of y is less than about 2.0 mm) ); and the number of voxels associated with the nodule candidate is greater than about 800.

3. An article of manufacture for analyzing volumetric chest computed tomography images for lung nodules, said article comprising:

a machine readable medium containing one or more programs which when executed implement the steps of;

obtaining the volumetric chest computed tomography images for lung nodules from an image acquisition device;

separating the lungs from other structures on the volumetric chest computed tomography images to form lung images;

detecting nodule candidates in the lung images with a local density maximum algorithm; and reducing false-positives among the detected nodule candidates based upon by an application of parameters concerning lung nodules.

4. An article of manufacture as defined in claim 3, wherein: the parameters include for each nodule candidate are:

a number of voxels associated with the nodule candidate;

ratio R1 defined as a volume of the nodule candidate over a volume of a modified bounding box of the nodule candidate;

ratio R2 defined as a maximal projection length of the nodule candidate along an axis of z over a maximal projection length of the nodule candidate, the maximal projection length being the larger of a projection length along the axis of x and a projection length along axis of y; and ratio R3 defined as the maximal projection length of the nodule candidate over the minimal projection length, the minimal projection length being the smaller is smaller the projection length along the axis of x and the projection length along axis of y; and deleting the nodule candidate from further consideration when one of the following criteria is established:

R1 is less than about 0.3;

R2 is greater than about 5.0;

R2 is less than about 0.2;

R3 is greater than about 1.5;

((the projection length along the axis of x is less than about 2.0 mm) AND (the projection length along axis of y is less than about 2.0 mm)); and the number of voxels associated with the nodule candidate is greater than about 800.

5. An apparatus for analyzing volumetric chest computed tomography images for lung nodules, said apparatus comprising:

an image analyzing unit configured to:

obtain the volumetric chest computed tomography images for lung nodules from an image acquisition device;

separate the lungs from other structures on the volumetric chest computed tomography images to form lung images;

detect nodule candidates in the lung images with a local density maximum algorithm; and reduce false-positives among the detected nodule candidates based upon by an application of parameters concerning lung nodules.

6. A method as defined in claim 5, wherein: the parameters include for each nodule candidate are:

a number of voxels associated with the nodule candidate;

ratio R1 defined as a volume of the nodule candidate over a volume of a modified bounding box of the nodule candidate;

ratio R2 defined as a maximal projection length of the nodule candidate along an axis of z over a maximal projection length of the nodule candidate, the maximal projection length being the larger of a projection length along the axis of x and a projection length along axis of y; and ratio R3 defined as the maximal projection length of the nodule candidate over the minimal projection length, the minimal projection length being the smaller is smaller the projection length along the axis of x and the projection length along axis of y; and the image analyzing unit is configured to delete the nodule candidate from further consideration when one of the following criteria is established:

R1 is less than about 0.3;

R2 is greater than about 5.0;

R2 is less than about 0.2;

R3 is greater than about 1.5;

((the projection length along the axis of x is less than about 2.0 mm) AND (the projection length along axis of y is less than about 2.0 mm)); and the number of voxels associated with the nodule candidate is greater than about 800.

7. A method for detecting lung nodule candidates in extracted lung images, said method comprising the steps of:

(a) selecting processing parameters which define:

a threshold step value;

a stop value;

an initial threshold level equal to the maximum voxel density value of the extracted lung images minus the threshold step value;

a minimal size of local maximum; and a minimal density peak height of local maximum;

(b) segmenting the extracted lung images at the threshold level;

(c) identifying three-dimensional (3D) objects at the threshold level;

(d) determining whether a previous object has been detected that overlaps with a current object and proceeding to step (f) when no previous object has been detected;

(e) determining local maxima at the threshold level based on an analysis of the previous object and current objects;

(f) saving the objects on a previous object array;

(g) reducing the threshold level by the threshold step value;

(h) repeating steps (b) through (g) provided that the threshold value is greater than the stop value.

8. A method as defined in claim 7, wherein step (c) comprises the substeps of:

(a) finding a plurality of segments of connected pixels having a value equal to 1 in a row of a plane;

(b) assigning a separate object number to each of said plurality of segments to define an object list;

(c) unifying the object number of each of said plurality of segments when it overlaps another of said plurality of segments in at least one of another row and plane;

(d) updating the object list;

(e) repeating substeps (a) through (d) for each row in the plane; and (f) repeating substep (e) for each plane.

9. A method as defined in claim 7, wherein step (e) comprises the substeps of:

(a) determining for each current object whether the current object has more than one previous object on the current object;

(b) proceeding to substep (j) when the current object does not have more than one previous object on the current object;

(c) determining for each current object whether local maxima have already been found on the previous object associated with the current object;

(d) proceeding to substep (h) when local maxima have already been found on the previous object;

(e) determining whether the previous object is a local maximum;

(f) proceeding to substep (i) when the previous objects are not a local maximum;

(g) marking the previous object as local maximum;

(h) marking the current object as a plateau;

(i) returning to step (f);

(j) determining whether there is only one previous object on the current object;

(k) proceeding to substep (i) when there is no previous object on the current object;

(l) determining whether the ratio of the object-to-box ratio of the previous object to that of the current object is larger than a specified value;

(m) proceeding to substep (i) when the object-to-box ratio is less than the specified value; and (n) proceeding to substep (c).

10. An article of manufacture for detecting lung nodule candidates in extracted lung images, said article comprising:

a machine readable medium containing one or more programs which when executed implement the steps of:

(a) selecting processing parameters which define:

a threshold step value;

a stop value;

an initial threshold level equal to the maximum voxel density value of the extracted lung images minus the threshold step value;

a minimal size of local maximum; and a minimal density peak height of local maximum;

(b) segmenting the extracted lung images at the threshold level;

(c) identifying three-dimensional (3D) objects at the threshold level;

(d) determining whether a previous object has been detected that overlaps with a current object and proceeding to step (f) when no previous object has been detected;

(e) determining local maxima at the threshold level based on an analysis of the previous object and current objects;

(f) saving the objects on a previous object array;

(g) reducing the threshold level by the threshold step value;

(h) repeating steps (b) through (g) provided that the threshold value is greater than the stop value.

11. An article of manufacture as defined in claim 10, wherein step (c) comprises the substeps of:

(a) finding a plurality of segments of connected pixels having a value equal to 1 in a row of a plane;

(b) assigning a separate object number to each of said plurality of segments to define an object list;

(c) unifying the object number of each of said plurality of segments when it overlaps another of said plurality of segments in at least one of another row and plane;

(d) updating the object list;

(e) repeating substeps (a) through (d) for each row in the plane; and (f) repeating substep (e) for each plane.

12. An article of manufacture as defined in claim 10, wherein step (e) comprises the substeps of:

(a) determining for each current object whether the current object has more than one previous object on the current object;

(b) proceeding to substep (j) when the current object does not have more than one previous object on the current object;

(c) determining for each current object whether local maxima have already been found on the previous object associated with the current object;

(d) proceeding to substep (h) when local maxima have already been found on the previous object;

(e) determining whether the previous object is a local maximum;

(f) proceeding to substep (i) when the previous objects are not a local maximum;

(g) marking the previous object as local maximum;

(h) marking the current object as a plateau;

(i) returning to step (f);

(j) determining whether there is only one previous object on the current object;

(k) proceeding to substep (i) when there is no previous object on the current object;

(l) determining whether the ratio of the object-to-box ratio of the previous object to that of the current object is larger than a specified value;

(m) proceeding to substep (i) when the object-to-box ratio is less than the specified value; and (n) proceeding to substep (c).

13. An apparatus for detecting lung nodule candidates in extracted lung images, said apparatus comprising:

a nodule detecting unit configured to:

(a) select processing parameters which define:

a threshold step value;

a stop value;

an initial threshold level equal to the maximum voxel density value of the extracted lung images minus the threshold step value;

a minimal size of local maximum; and a minimal density peak height of local maximum;

(b) segment the extracted lung images at the threshold level;

(c) identify three-dimensional (3D) objects at the threshold level;

(d) determine whether a previous object has been detected that overlaps with a current object and proceeding to step (f) when no previous object has been detected;

(e) determine local maxima at the threshold level based on an analysis of the previous object and current objects;

(f) save the objects on a previous object array;

(g) reducing the threshold level by the threshold step value;

(h) repeat steps (b) through (g) provided that the threshold value is greater than the stop value.

14. An apparatus for detecting lung nodule candidates as defined in claim 13, wherein the nodule detecting unit identifies three-dimensional (3D) objects at the threshold level by being configured to:

(a) find a plurality of segments of connected pixels having a value equal to 1 in a row of a plane;

(b) assign a separate object number to each of said plurality of segments to define an object list;

(c) unify the object number of each of said plurality of segments when it overlaps another of said plurality of segments in at least one of another row and plane;

(d) update the object list;

(e) repeat (a) through (d) for each row in the plane; and (f) repeat (e) for each plane.

15. An apparatus for detecting lung nodule candidates as defined in claim 13, wherein the nodule detecting unit analyses of the previous object and current objects to determine the local maxima at the threshold level by being configured to:

(a) determine for each current object whether the current object has more than one previous object on the current object;

(b) proceed to substep (j) when the current object does not have more than one previous object on the current object;

(c) determine for each current object whether local maxima have already been found on the previous object associated with current object;

(d) proceed to substep (h) when local maxima have already been found on the previous object;

(e) determine whether the previous object is a local maximum;

(f) proceed to substep (i) when the previous objects are not a local maximum;

(g) mark the previous object as local maximum;

(h) mark the current object as a plateau;

(i) return to step (f);

(j) determine whether there is only one previous object on the current object;

(k) proceed to substep (i) when there is no previous object on the current object;

(l) determine whether the ratio of the object-to-box ratio of the previous object to that of the current object is larger than a specified value;

(m) proceed to substep (i) when the object-to-box ratio is less than the specified value; and (n) proceed to substep (c).

* * * * *